United States Patent
Richter et al.

(10) Patent No.: US 7,178,418 B2
(45) Date of Patent: Feb. 20, 2007

(54) SEGMENT OF A SENSOR-SUPPORTING ELEMENT FOR A SCRAPER-TYPE DEVICE

(75) Inventors: Thomas Richter, Linkenheim (DE); Axel Schwarz, Weingarten (DE); Christiane Veit, Karlsruhe (DE)

(73) Assignee: NDT Systems & Services AG, Stutensee (DE)

( * ) Notice: Subject to any disclaimer, the term of this patent is extended or adjusted under 35 U.S.C. 154(b) by 84 days.

(21) Appl. No.: 10/507,297

(22) PCT Filed: Mar. 8, 2003

(86) PCT No.: PCT/EP03/02380

§ 371 (c)(1),
(2), (4) Date: Feb. 14, 2005

(87) PCT Pub. No.: WO03/076841

PCT Pub. Date: Sep. 18, 2003

(65) Prior Publication Data

US 2005/0126316 A1 Jun. 16, 2005

(30) Foreign Application Priority Data

Mar. 12, 2002 (DE) .............................. 102 10 746

(51) Int. Cl.
*B08B 9/27* (2006.01)
*G01B 7/12* (2006.01)
(52) U.S. Cl. ............... 73/866.5; 73/865.8; 15/104.03; 15/104.05; 15/104.063; 137/15.07

(58) Field of Classification Search .................. 73/431, 73/865.8, 866.6; 137/15.07, 15.11; 15/104.03, 15/104.05, 104.063
See application file for complete search history.

(56) References Cited

U.S. PATENT DOCUMENTS

| | | | | |
|---|---|---|---|---|
| 3,882,606 | A * | 5/1975 | Kaenel et al. ................ 33/544 |
| 4,072,894 | A * | 2/1978 | Barton ....................... 324/221 |
| 4,085,510 | A * | 4/1978 | Kirschke ................... 33/544.3 |
| 4,105,972 | A * | 8/1978 | Smith ........................ 324/220 |
| 4,249,810 | A * | 2/1981 | O'Connor et al. ............ 396/19 |
| 5,018,451 | A * | 5/1991 | Hapstack ................. 104/138.2 |

(Continued)

FOREIGN PATENT DOCUMENTS

CA 2 339 679 A1 2/2000

(Continued)

*Primary Examiner*—Hezron Williams
*Assistant Examiner*—David A. Rogers
(74) *Attorney, Agent, or Firm*—Rothwell, Figg, Ernst & Manbeck

(57) ABSTRACT

Disclosed is a segment (15) of a sensor-supporting element for a scraper-type device, which comprises at least two pairs of runners (16a, 16b) that are arranged essentially parallel behind each other. A support plate (20) receiving sensors (21) is disposed between at least one pair of runners (16). The segment (15) can be combined with other such segments (15) so as to form a sensor-supporting element.

44 Claims, 22 Drawing Sheets

U.S. PATENT DOCUMENTS

Figure 1:
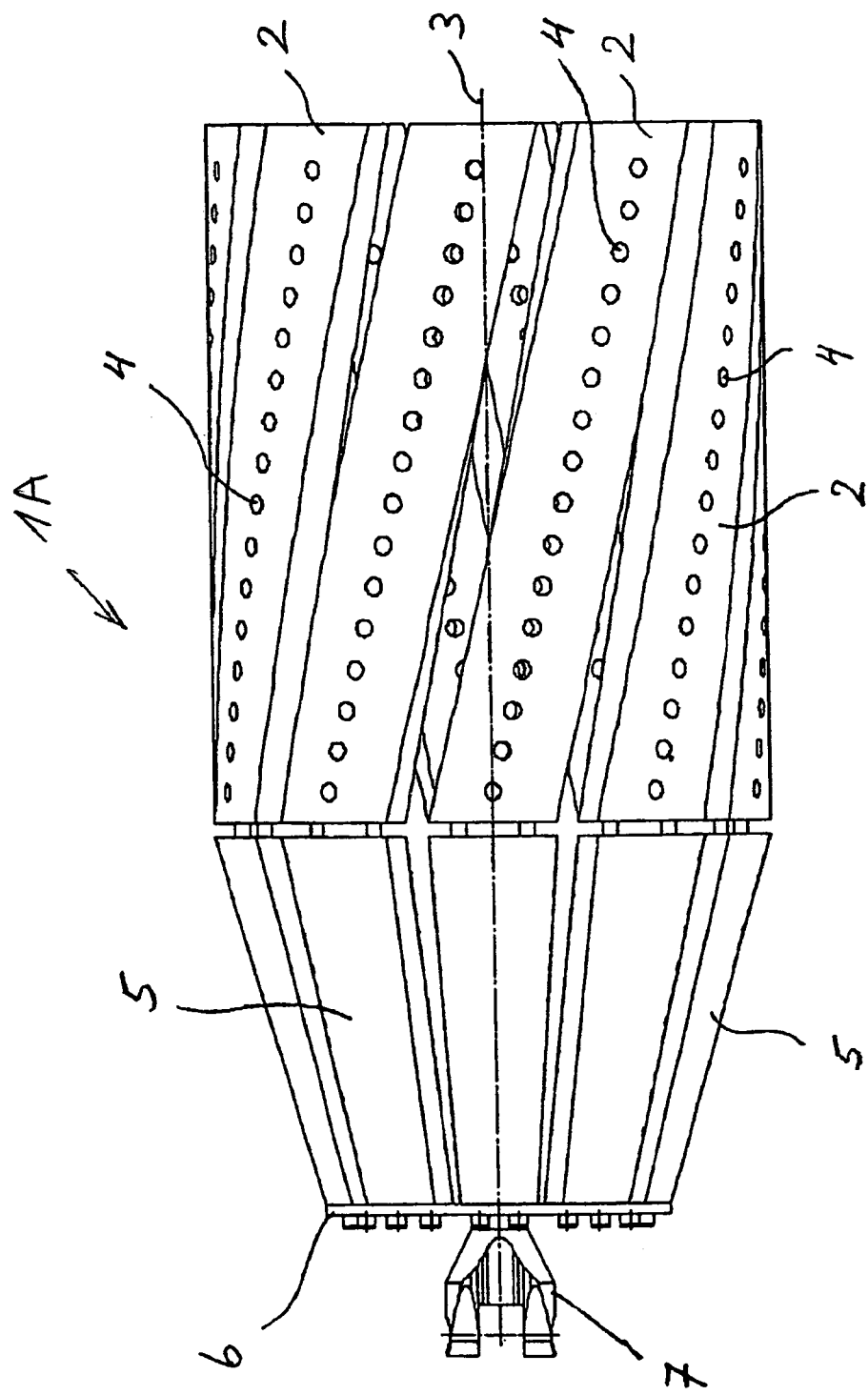

| | | | |
|---|---|---|---|
| 5,371,363 A * | 12/1994 | Lilimpakis | 250/253 |
| 5,398,560 A * | 3/1995 | Zollingger et al. | 73/865.8 |
| 5,454,276 A * | 10/1995 | Wernicke | 73/865.8 |
| 5,616,854 A | 4/1997 | Berg | |
| 5,864,232 A * | 1/1999 | Laursen | 324/200 |
| 6,100,684 A * | 8/2000 | Ramaut | 324/220 |
| 6,107,795 A * | 8/2000 | Smart | 324/220 |
| 6,232,773 B1 * | 5/2001 | Jacobs et al. | 324/220 |
| 6,339,993 B1 * | 1/2002 | Comello et al. | 104/138.2 |
| 6,381,797 B1 * | 5/2002 | Filippovitch et al. | 15/104.061 |
| 6,450,104 B1 * | 9/2002 | Grant et al. | 104/138.2 |
| 6,500,271 B1 * | 12/2002 | Moore et al. | 134/8 |
| 2002/0190682 A1 * | 12/2002 | Schempf et al. | 318/568.11 |
| 2003/0089267 A1 * | 5/2003 | Ghorbel et al. | 104/138.1 |
| 2004/0112152 A1 * | 6/2004 | Stout et al. | 73/865.8 |

FOREIGN PATENT DOCUMENTS

| | | | |
|---|---|---|---|
| DE | 36 26 646 A1 | | 2/1988 |
| JP | 63253249 A | * | 10/1988 |
| WO | WO 00/08377 A1 | | 2/2000 |
| WO | WO 00/08378 A1 | | 2/2000 |

* cited by examiner

Fig. 2 "Prior Art"

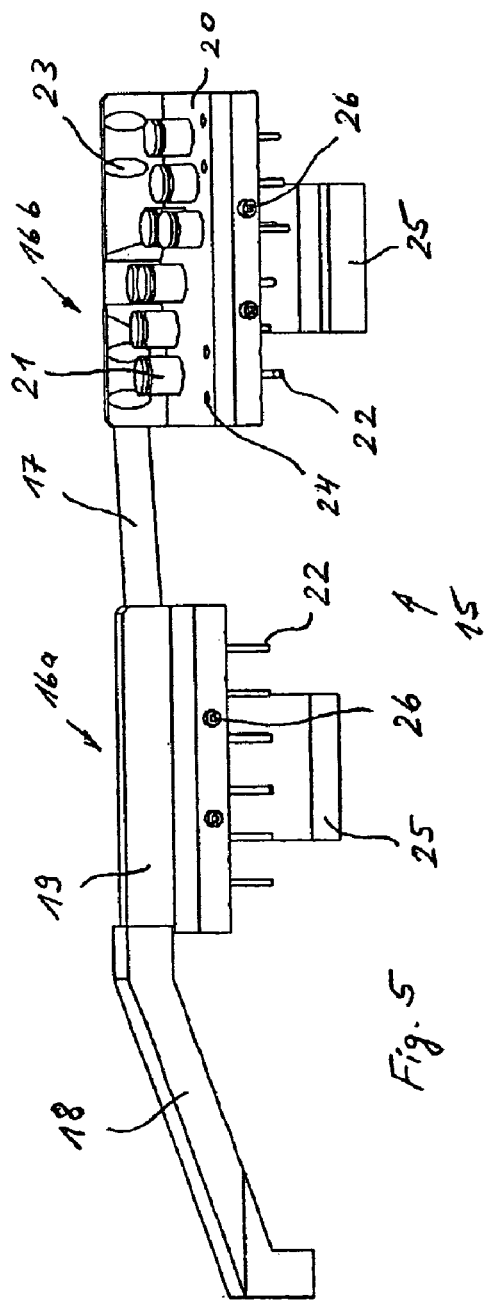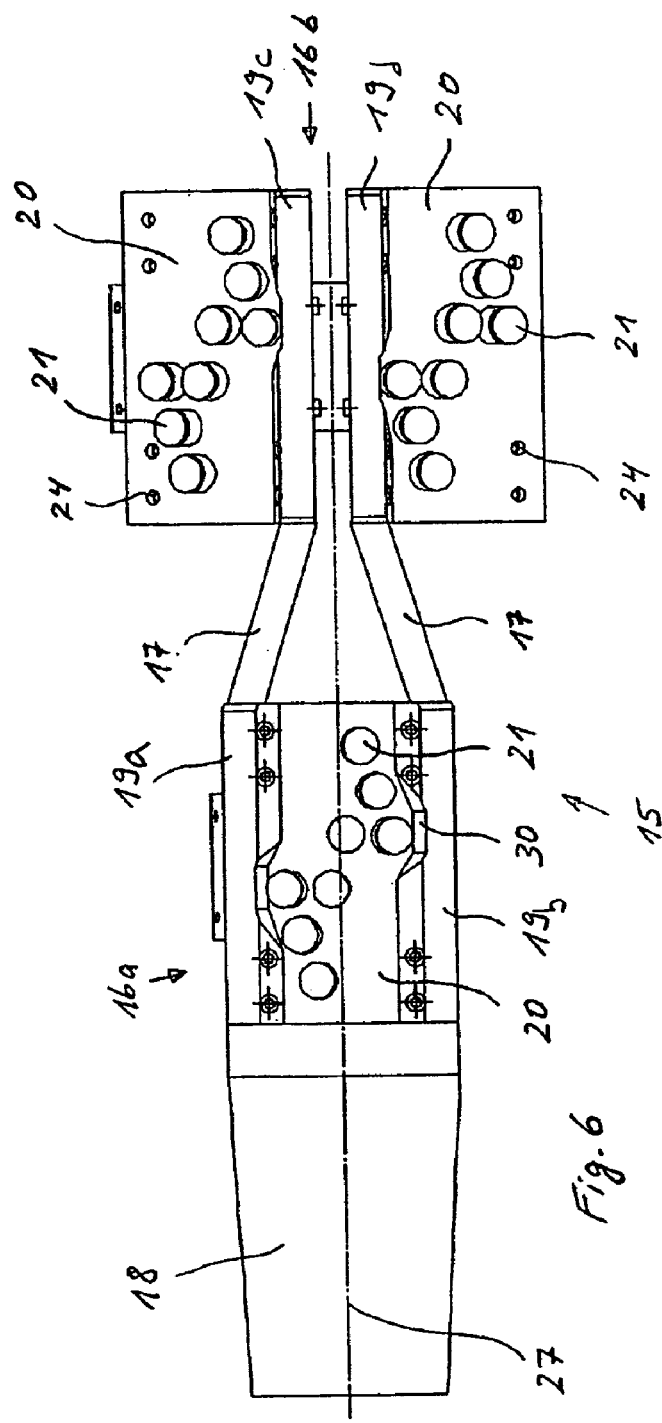

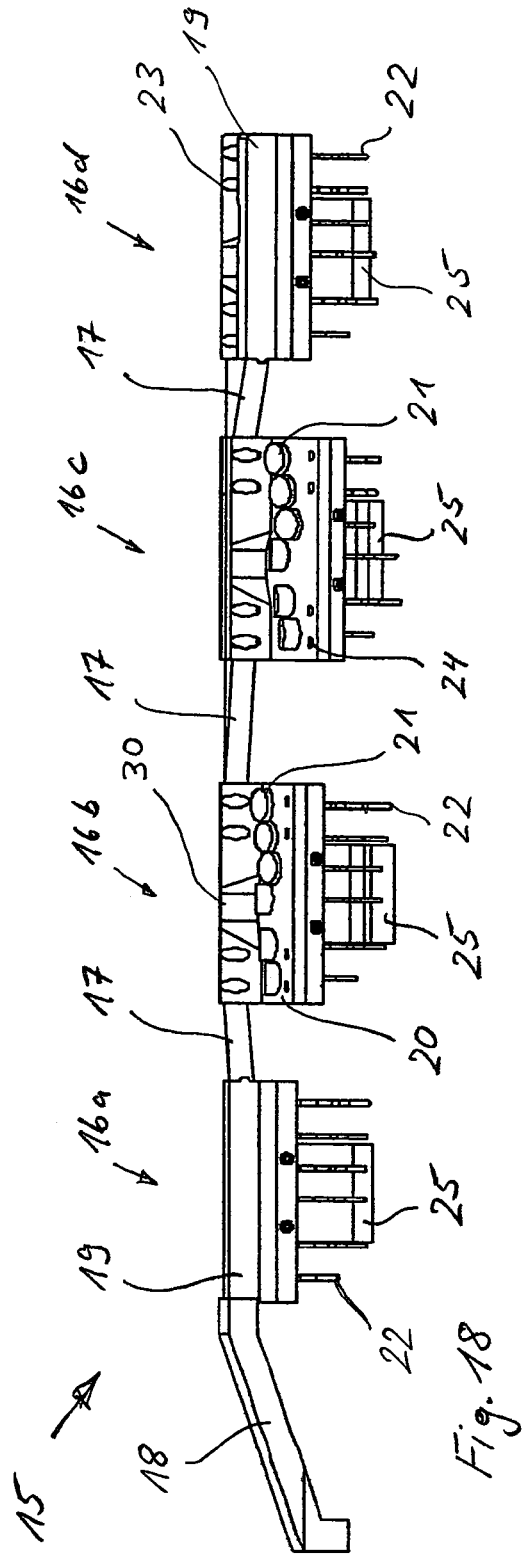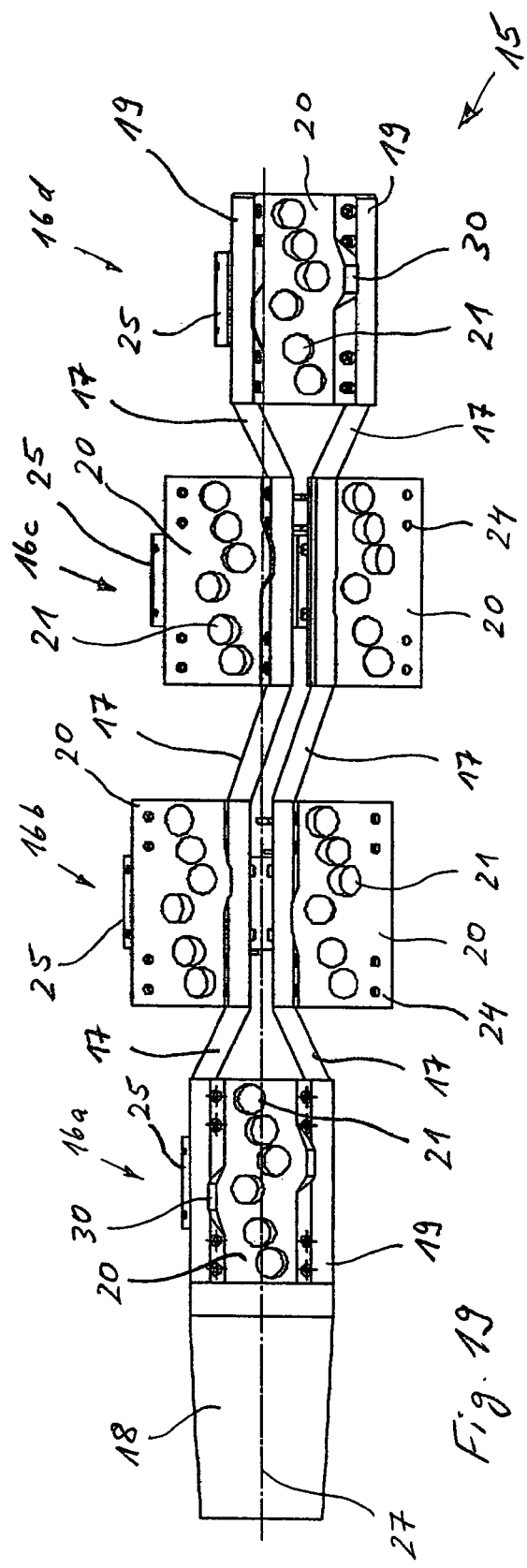

SEGMENT OF A SENSOR-SUPPORTING ELEMENT FOR A SCRAPER-TYPE DEVICE

CROSS REFERENCE TO RELATED APPLICATION

This application is a 35 U.S.C. § 371 National Phase Entry Application from PCT/EP03/02380, filed Mar. 8, 2003, and designating the U.S.

The invention relates to a segment for a sensor-supporting element of a scraper-type device, in which the sensor-supporting element is assembled from segments and forms a hollow body with a cylindrical enveloping surface and the scraper-type device can be moved through a pipeline for the purpose of pipeline testing, whereby the sensor-supporting element is fitted with sensors required for pipeline testing. Scraper-type devices of this type are moved through pipelines in order to perform measurements and non-destructive materials testing. They usually comprise a sensor-supporting element fitted with the sensors required for pipeline testing and one or several additional scraper-type device elements containing devices for recording and processing measured values as well as the power supply facility.

Scraper-type devices are employed in long-distance pipelines, such as oil pipelines, to detect damage on the pipe wall, such as the formation of corrosion, fissures or pitting. It is the task of the scraper-type device to obtain detailed information about the type, extent and location of damage on the internal wall, in the material or on the external wall of the pipe. For this purpose, the sensors of the scraper-type device scan the entire circumference of the internal pipe wall while the scraper-type device is being moved through the pipeline. Usually, the scraper-type device is moved by means of the medium which is transported through the pipeline. Sensors with various operating principles, such as ultrasound or electromagnetic sensors, are employed for pipeline testing. It is an object of the sensor-supporting element to guide the sensors in a certain position of or at a certain distance to the internal pipe wall.

Various types of sensor-supporting elements for scraper-type device are known. A known embodiment uses sensor-supporting elements, in which the sensors are arranged on segments forming separate segment rings which are arranged behind each other (sequential arrangement). The segment rings are connected to each other by means of a rigid axis which is oriented in the direction of motion of the scraper-type device. The main disadvantage of this design is the low adaptability of the sensor-supporting element with regard to pipe curvature because of its rigid axis, and the resulting large overall length of the sensor-supporting element.

Moreover, sensor-supporting elements are known, in which the sensors are connected to a supporting element by means of extensive mechanical devices, such as a linkage of bars, in order to ensure that the individual sensors are positioned at a largely identical distance from the internal pipe wall while the sensor-supporting element is being moved through the pipeline. A disadvantage of this type of mechanical device is their strong susceptibility to failure which interferes with the measuring accuracy of the sensors.

Another known embodiment utilizes runners which are twisted in longitudinal direction. The sensors are arranged behind each other in the runners and the twist of the runners provides for a lateral offset of the sensors which thus cover the entire circumference. This arrangement is disadvantageous in that the forward-facing side edges of the twisted runners, each of which covers a large fraction of the circumference of the pipe, can scrape-of contamination from the pipe wall and generate forces aiming to straighten the runners. Both interferes with the testing results, e.g. by the sensors becoming plugged with wax or by sensor positioning errors. Since the offset of the sensors is effected by the twist of the runners, shorter overall lengths can be achieved only by increasing the twist of the runners. Because of the associated disadvantages, it is not possible to implement the sensor-supporting element with a short overall length and thus the arc-traversing properties are fairly poor.

A sensor-supporting element provided in the form of a cuff is known from DE 3626646 C2. The cuff is subdivided into parallel strip segments, in which the sensors are arranged. If the strip segments are oriented parallel to the axis of the scraper-type device, it is hardly possible to provide for overlap of the measuring areas scanned by the sensors or for offset of the sensors in the direction of the circumference. Therefore, in a preferred embodiment of this sensor-supporting element, the middle axes of the parallel strip segments form an acute angle with the middle axis of the pipeline, which provides for offset of the sensors in the direction of the circumference such that sequentially arranged sensors of a strip segment scan a strip of the surface of the pipe wall that is wider than the effective scanning area of an individual sensor. This arrangement is disadvantageous in that, while moving through the pipeline, realigning forces act on the strip segments, which are skewed relative to the direction of motion of the scraper-type device, such as to realign the strip segments parallel to the middle axis of the pipeline. This not only jeopardizes the desired measuring accuracy, but also leads to scraping on contaminations or uneven spots of the pipe wall and therefore to additional interference with the measuring results or to damage of the scraper-type device.

From U.S. Pat. No. 5,616,854, a device for pneumatic leakage testing of pipelines is known, in which a cuff is placed on the outside of the pipeline to be tested.

The object of the present invention on the basis of the prior art is to provide a segment of a sensor-supporting element of a scraper-type device as quoted above, which can be assembled together with other identical segments to form a sensor-supporting element which is characterized by its high operating and functional safety and good arc-traversing properties. The present invention further relates to a sensor-supporting element or scraper-type device assembled accordingly.

This object is met by the present invention by a segment with the features of the attached Claim 1. Preferred developments and further refinements of the invention are evident from the dependent patent claims and the following description and accompanying drawings.

A segment according to the invention therefore comprises at least two pairs of runners, each consisting of two essentially parallel runners. The pairs of runners are arranged behind each other (sequential arrangement) against the direction of motion of the scraper-type device. The runners are aligned in the direction of motion of the scraper-type device, i.e. in longitudinal direction of the segment. The sequentially arranged runners are connected elastically to one another by means of connecting elements. The elastic connection, e.g. made from an elastic material, preferably from a plastic material, or effected by means of metallic spring elements of the runners provides for the runners to be capable of adapting to uneven spots of the internal pipe wall, such as dents, such that the sensor-supporting element as a whole can balance out variations of the diameter of the tested pipeline, whereby the upper side of the runners touches the internal pipe wall at all times and the runners guide the sensors at their nominal distance to the pipe wall.

A sensor support plate for sensors is arranged between the runners of at least one pair of runners. The support plate can be attached to the runners as a separate part or provided in the form of the same part as the runners.

The segment is provided such that it can be connected to additional such segments by means of a segment-connecting connecting device to form a hollow body with a cylindrical envelope surface.

A segment according to the invention can be used to form a sensor-supporting element of a scraper-type device which has high operating and functional safety, guides the sensors at a defined position relative to the internal pipe wall, is flexible such that variations of the pipe diameter are compensated and the arrangement is enabled to yield at uneven spots of the internal pipe wall to reduce wear and tear, is compact and short in overall length, which improves the arc-traversing properties, can be moved by the scraper-type device without generating transverse forces or straightening forces acting on the segments effectively such that the measuring accuracy is high and the abrasion on the pipe and segments is low, and can be assembled, disassembled, and serviced easily due to its structure.

The feature of the runners being essentially parallel to each other means that the angle between the runners is less than 15°, preferably less than 10° and particularly preferably less than 5°. In this type of straight orientation, the advantages of the invention with regard to low scraping effect and short overall length are retained.

The straight orientation of the runners minimizes the risk of contamination due to scraping. Consequently, the sensors can be installed in the support plates in any arrangement such that a compact design and overlapping scanning areas for improving the measuring accuracy can be realized.

The invention does not require the runners to be twisted in order to attain the offset of the sensors, and the sensors can be installed in any arrangement and with a compact design on the support plates. This results in short overall length, good arc-traversing properties, and low scraping effect.

The runners themselves can consist of a relatively firm, inelastic material, if high intrinsic stability of the runners is desired. In this case, the elasticity of the sensor-supporting element is attained essentially by means of the elastic connecting elements between the runners and/or segments. In a preferred embodiment, the runners consist of elastic material, preferably the same material as the connecting elements, in particular if provided in the form of a single part, in order for the segments to attain high flexibility. The runners can also be provided with reinforcing elements, if required, if the stability attained by being connected to the support plates is insufficient.

In a further preferred embodiment, at least one additional support plate for sensors can be attached between a runner of one segment and a runner of a neighboring segment. The segments of a sensor-supporting element can be connected by means of support plates, which are arranged between the segments, to form the sensor-supporting element. In another preferred embodiment of the segment, the connecting device can be attached in the front side of the segment facing in the direction of motion of the scraper-type device. The connecting device is preferably provided in the form of a flange connecting the front sides of the segments. U-shaped spring plates arranged between neighboring segments are another preferred embodiment of a connecting device.

The number of pairs of runners consisting of two parallel runners of a segment each is preferably between two and ten, particularly preferably between two and four. Amongst other factors, the number depends on the number of support plates for sensors required to attain a certain measuring accuracy, and on the desired arc-traversing properties of the sensor-supporting element.

In an advantageous embodiment, the front side of a segment facing in the direction of motion of a scraper-type device is provided conical-tapering, e.g. in the form of a conical-tapering section of the segment, such that the cylindrical hollow body assembled from the segments possesses a truncated cone-like section at its front side. This allows the hollow body, which serves as the sensor-supporting element, to be pulled through a pipeline without any trouble even if the pipeline's cross-section is reduced by uneven spots in the pipe wall, such as dents.

The sequentially arranged pairs of runners are advantageously connected to each other by means of elastic interim segments, which are preferably arranged at the runners at an angle and preferably have a round, oval, rectangular or trapezoidal cross-section. The cross-section of the interim segments can be smaller than the cross-section of the runners in order to improve the elastic resiliency of the segments. The interim segments can be parallel or converge or diverge with respect to each other, whereby the interim segments of different pairs of runners of a segment can differ in their respective arrangement.

The elastic interim segments provide for the sequentially arranged pairs of runners to be arranged as close to parallel to the pipe axis as possible and for the runners to be capable of adapting to variations in diameter and uneven spots. Moreover, using these elastic interim segments and selecting a small overall length for a sensor-supporting element assembled from segments according to the invention provides for a crucial improvement in the arc-traversing properties of the sensor-supporting element such that pipeline sections with strong pipe curvature and a small radius of curvature can be traversed also.

The features illustrated in the following may be advantageous in order to improve the stability of the sensor-supporting element, increase the stability of the segments and the sensor-supporting element with regard to pulling forces, e.g. in order to prevent that segments are pulled off or damaged by abrupt forces acting when exits protruding into the pipe are traversed, and to improve the steering stability of the sensors during their movement through the pipe.

According to a first advantageous feature it is proposed that the segment between at least one pair of runners comprises at its front side with regard to the direction of motion of the scraper-type device a transverse fin part connecting the runners of the pair of runners. According to another advantageous feature the segment comprises between the support plate, which is attached between a pair of runners, and a runner of a trailing (relative to the direction of motion) pair of runners a connecting element connecting the support plate and the runner. Preferably, the connecting element is arranged along the longitudinal direction of the runner and the connecting elements between a support plate and a runner are attached to the support plate by means of sleeves.

According to yet another advantageous feature it is proposed that the segment comprises a transverse fin part allowing it to be connected to a neighboring segment. Moreover, the transverse fin part can be provided such that it can be connected to a corresponding transverse fin part of a neighboring segment such that the two transverse fin parts complement each other to form a transverse fin connecting neighboring segments.

In this context, an interim segment for connecting two sequential runners can be coupled to the transverse fin part of a segment by means of a sleeve. The sleeve provides for a pulling force-resistant, but flexible connection.

The length of the runners is preferably between 5 cm and 300 cm, and particularly preferably between 10 cm and 50 cm. It depends on the preferred length of the attachable support plates and the required arc-traversing properties of the runners and sensor-supporting element. With decreasing length of the runners, their arc-traversing properties improve, but the length of the support plates which can be attached between the runners, and therefore the number of sensors which can be fitted on a support plate decreases.

The length of interim segments connecting sequentially arranged runners to each other is preferably between 2 cm and 50 cm. In a preferred embodiment of a segment according to the invention, all runners are of uniform length. It is also possible for all interim segments connecting adjacent runners to be of the same length. This does not only reduce the manufacturing costs, but also causes the segment to show uniform mechanical behavior along its entire length.

The ratio of the length of the interim segments to the length of the adjacent runners which are connected by the interim segments is preferably between 1/10 and 5, particularly preferred is a ratio between 2/10 and 1. In this regard, it must be taken into consideration, that, on the one hand, the overall length of the segment or sensor-supporting element is reduced by the length of the interim segments being small, but, on the other, interim segments with a greater length increase the flexibility of the segment or sensor-supporting element, with both factors being beneficial for the arc-traversing properties.

In order to increase the stability of the runners, they can be provided to advantage to possess a trapezoidal, parallelogram-like or rectangular cross-section. Also influencing the stability is the ratio of the height of the runner, i.e. the dimension of the runner in a direction radial to the sensor-supporting element assembled from the segments according to the invention, relative to the width of the runner, i.e. the dimension of the runner in the direction of the circumference of the sensor-supporting element, and a preferred ratio is between 1/3 and 3.

The upper side of the runners can be level or, preferably, curved in a direction transverse to their longitudinal direction, which corresponds to the direction of motion of the scraper-type device. A level shape is useful for small runners or small pipe diameters, whereas a curved upper side is advantageous in particular in the case of broad runners or large pipe diameters. It is preferable for the radius of curvature of the curved upper sides to be adapted to radius of the cylindrical envelope surface of the sensor-supporting element assembled from segments according to the invention such that the runners of a sensor-supporting element touch the internal pipe wall to the extent possible while the sensor-supporting element is being moved through the pipe. To reduce the friction between the runners and the internal pipe wall and, therefore, to reduce the abrasion and increase the serviceable life of the runners, abrasion-resistant shoes made from a metallic material and ending flush with the surface of the runners can be incorporated into the runners at regular spaces. In addition, abrasion-resistant shoes also increase the stability of the runners. It is preferable for a runner to be fitted with incorporated abrasion-resistant shoes over between 1/10 and 3/4 of its length.

The runners can be provided with recesses, for example between the abrasion-resistant shoes. Recesses of this type are particularly advantageous to generate a clearance for the measuring field of the sensors, e.g. ultrasound sensors emitting ultrasound in a skewed direction.

The support plates for sensors can be attached to the underside of the runners. This increases the stability of the segment and therefore the stability of the sensor-supporting element. In this context, the runners can comprise bores to receive screws, whereas the support plates are fitted with internal threads matching these screws such that the support plates can be screwed to the runners. This renders not only the assembly of the segment and sensor-supporting element simple, but also the replacement of segments, support plates and sensors for repair purposes.

The support plates can be arched or level, which is preferable in order to save manufacturing costs. If there is a requirement to keep the distance between the sensors and the internal pipe wall constant, this can be satisfied by suitably adjusting the assembled height of the sensors.

Preferably, the undersides of the runners are also level in shape and beveled such that they are adapted to the orientation in radial direction relative to the sensor-supporting element of the support plates, which are to be attached.

A segment according to the invention can be provided fully or essentially in the form of a single part. It is preferable for the single part to comprise especially one or several of the following components: runners, elastic connecting elements, interim segments, conical-tapering segment section, transverse fin parts. Providing these components in the form of a single part simplifies the manufacture.

It is preferable for the segment or parts thereof, especially a part comprising multiple components, to consist of an elastic plastic material, which, on the one hand, is sufficiently elastic to allow for flexibility, especially of the connecting elements of the interim segments, and, on the other hand, is sufficiently resistant and stable for the segments, especially the runners, to fulfill their task of guiding the sensors. In practical application, elastic plastic materials with a Shore A hardness of 65 to 95 have proven advantageous. For example polyurethane is a suitable material.

Multiple segments according to the invention can form a sensor-supporting element in the form of a cylindrical hollow body of a scraper-type device. It is preferable for the sensor-supporting element to be assembled from individual segments, but it can also be provided in the form of a single part. U-shaped spring plates can be attached between neighboring segments of such a sensor-supporting element in order to pre-tension the sensor-supporting element such that the runners of the segments are pressed against the internal pipe wall of the pipe, in which the sensor-supporting element is being moved. It is preferable for these U-shaped spring plates to be attached to the support plates, which in turn are attached to the underside of the runners. A scraper-type device comprising at least one sensor-supporting element according to the invention can be moved through pipelines in order to perform measurements and non-destructive material testing.

Figure 2:
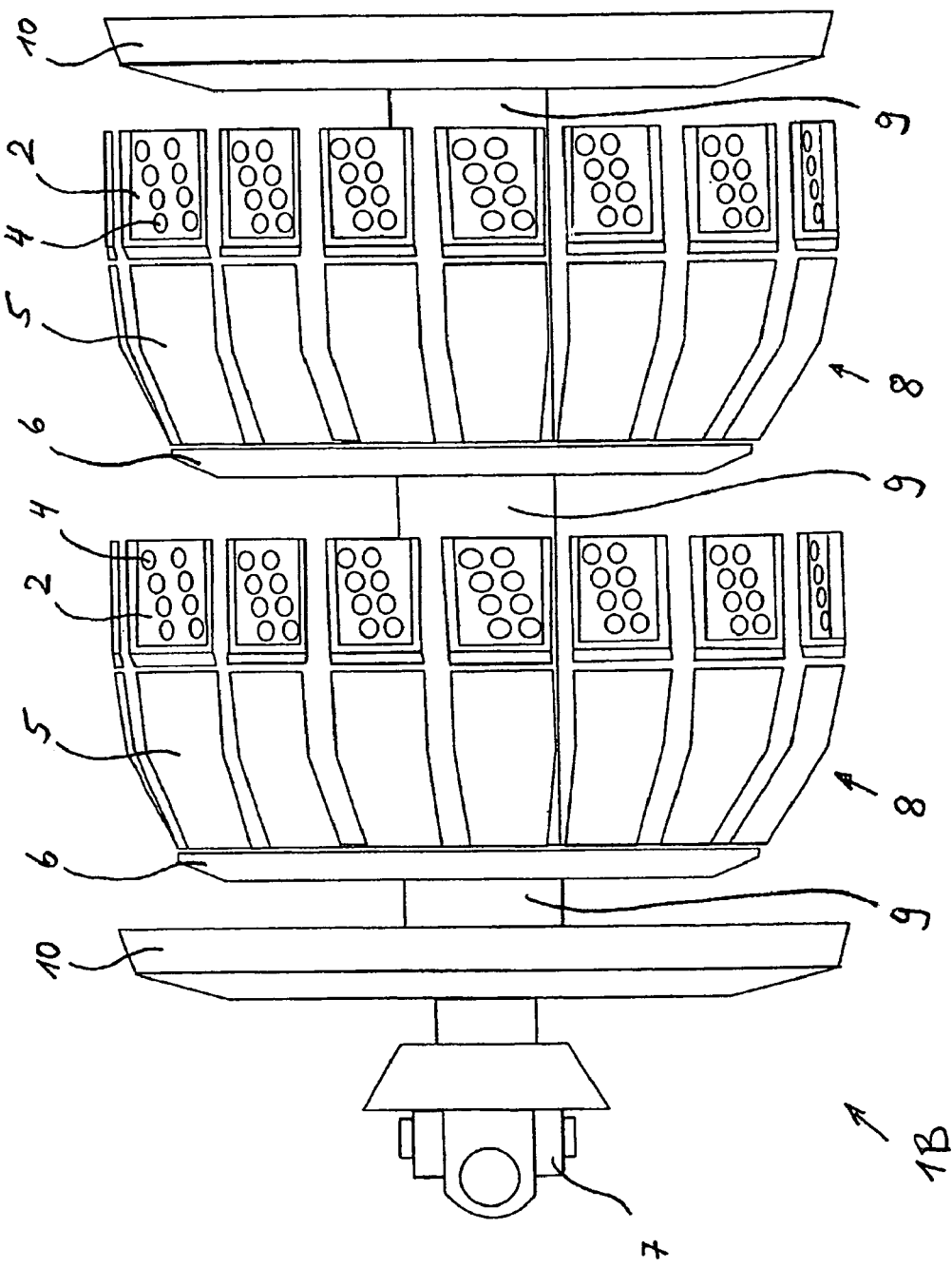
Figure 3:
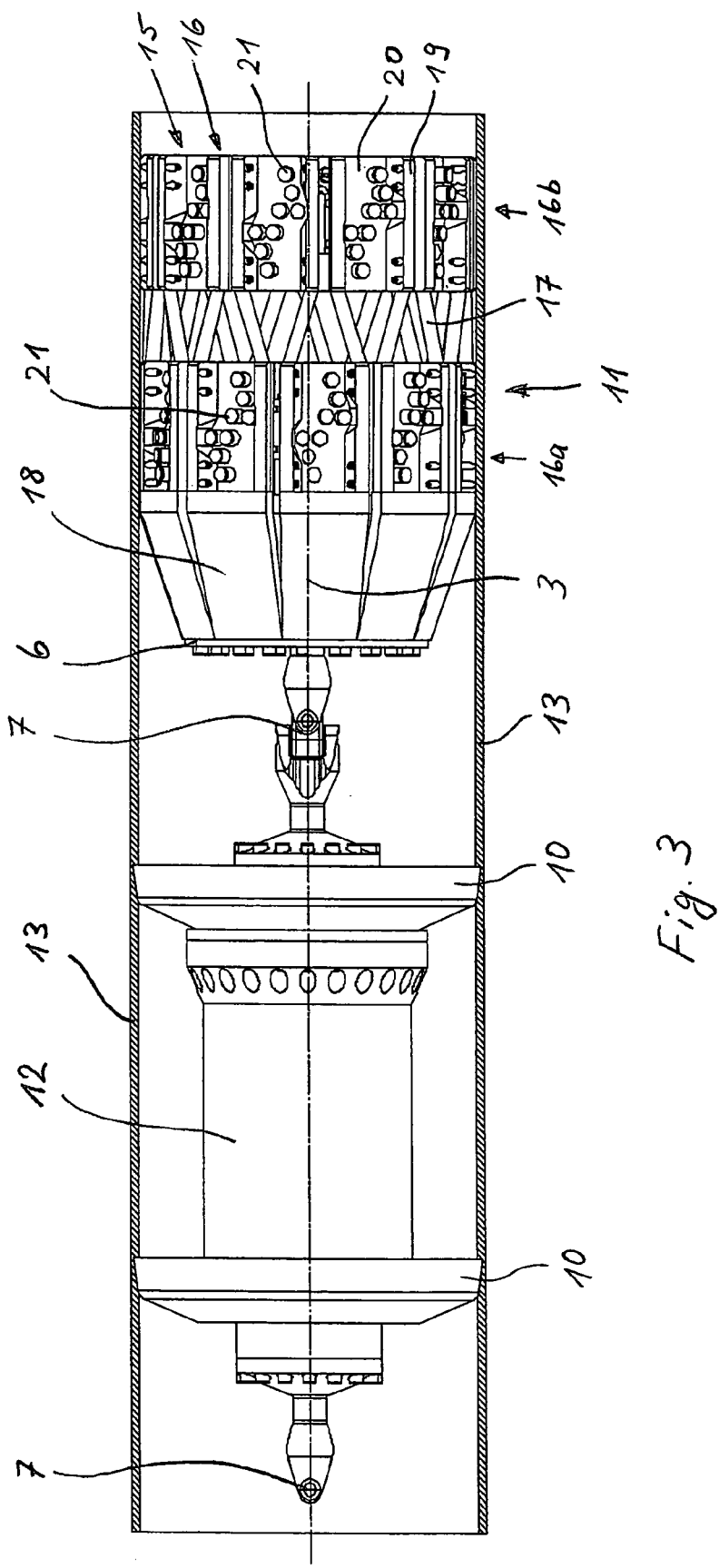
Figure 4:
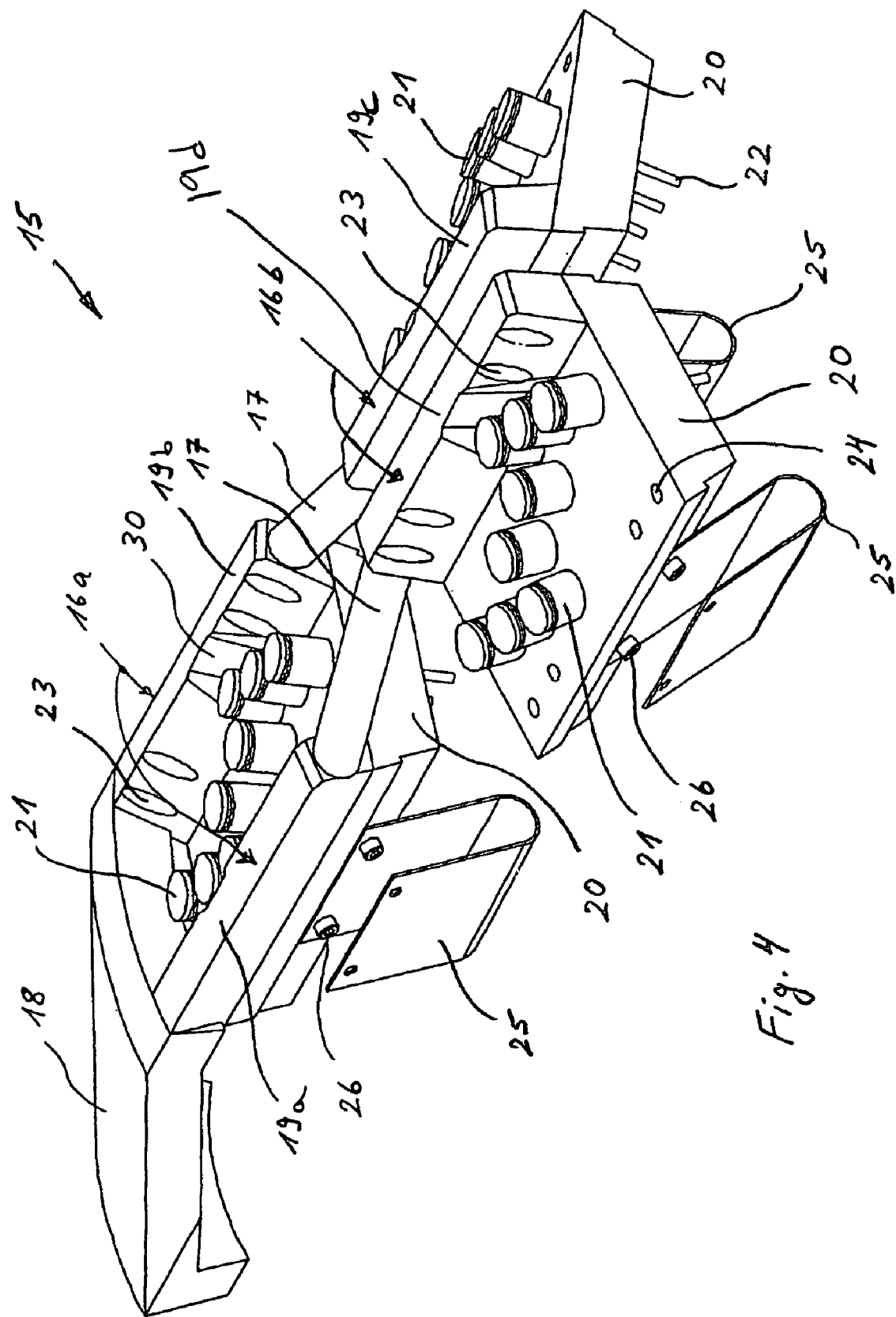
Figure 7:
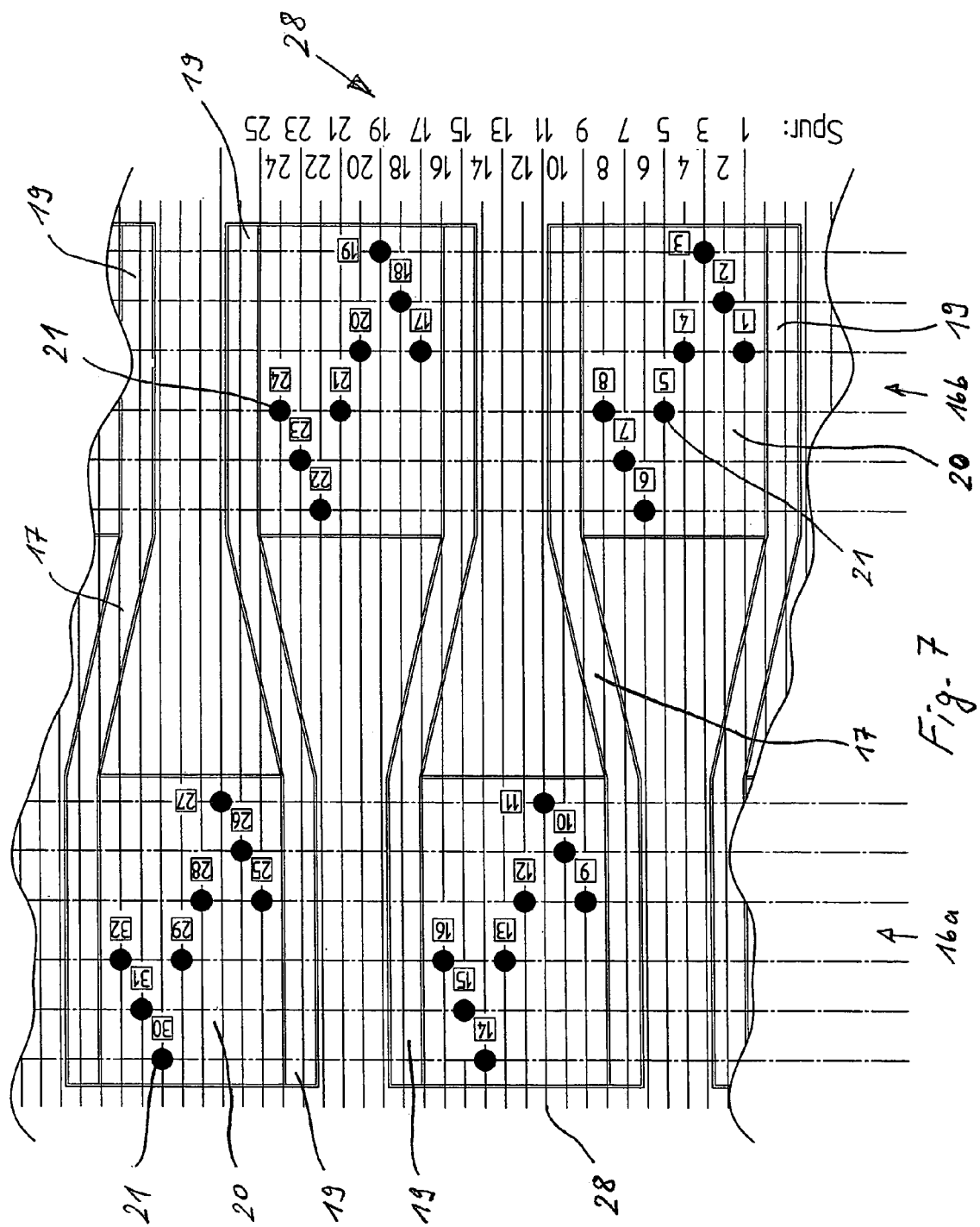
Figure 8:
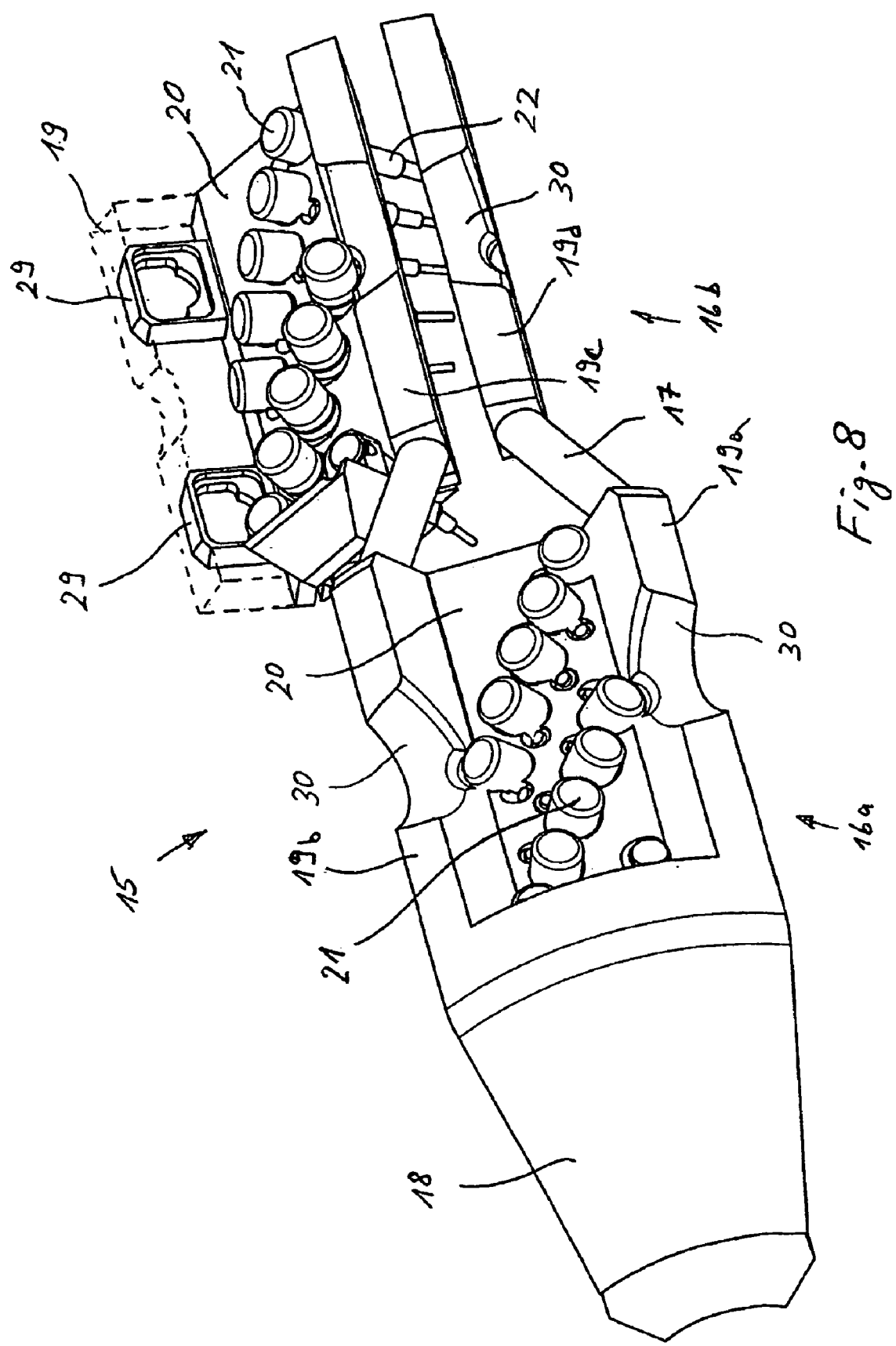
Figure 9:
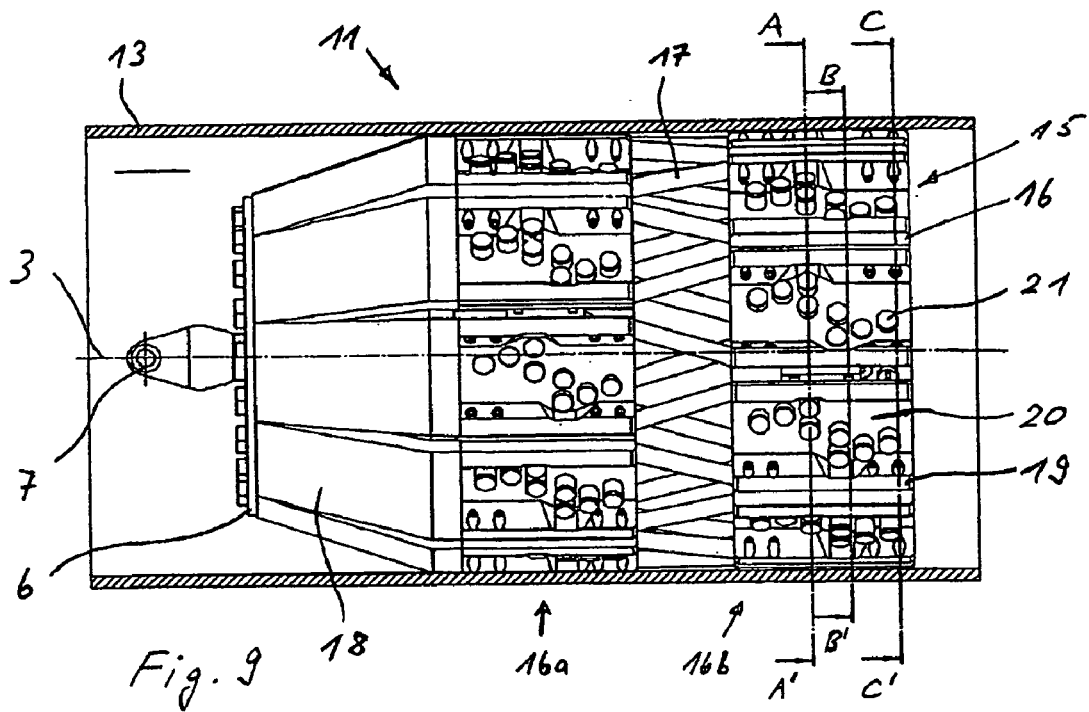
Figure 10:
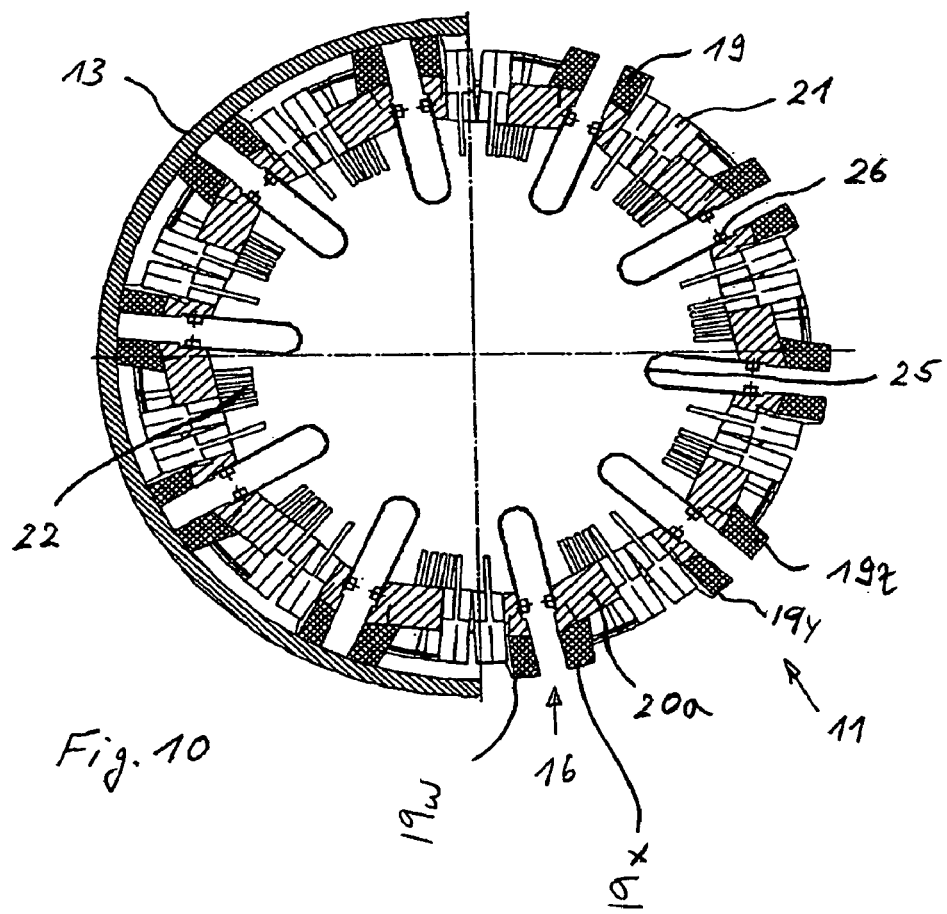
Figure 11:
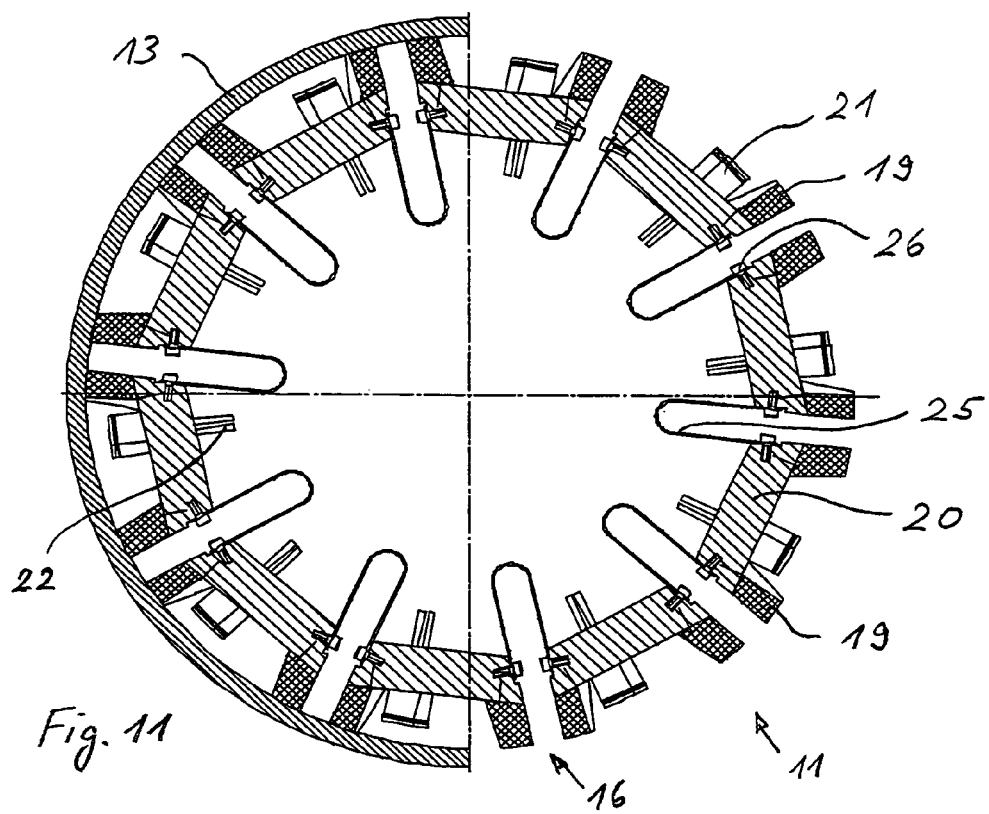
Figure 12:
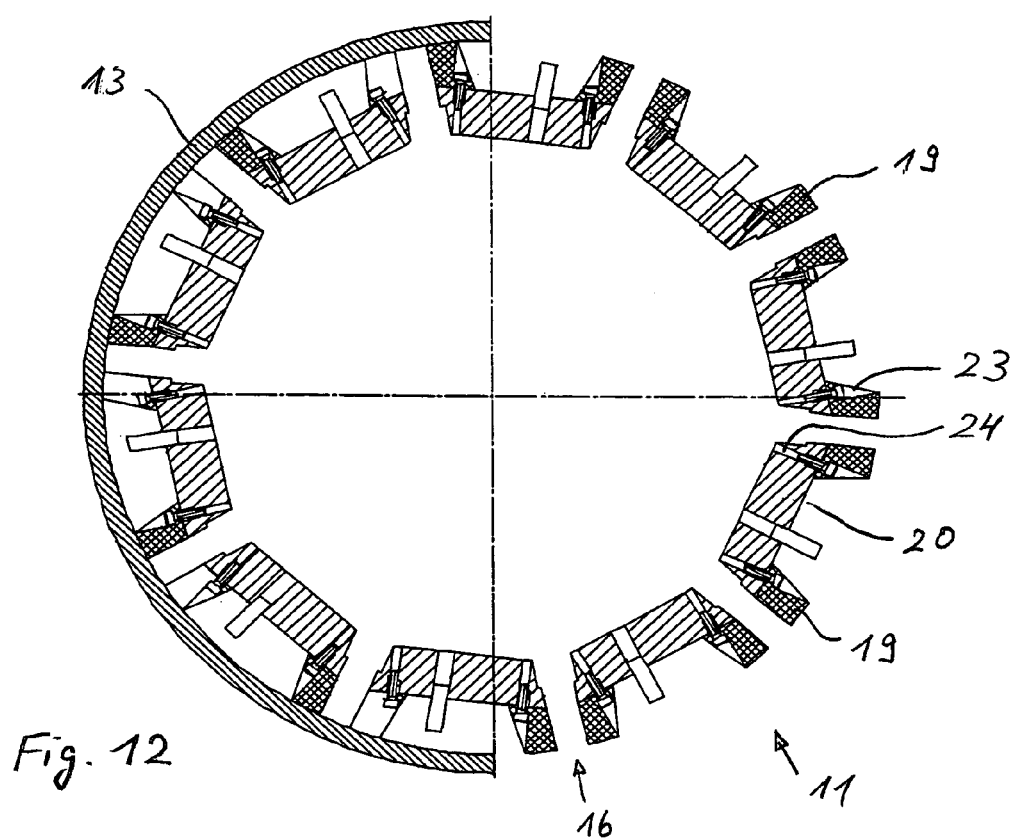
Figure 13:
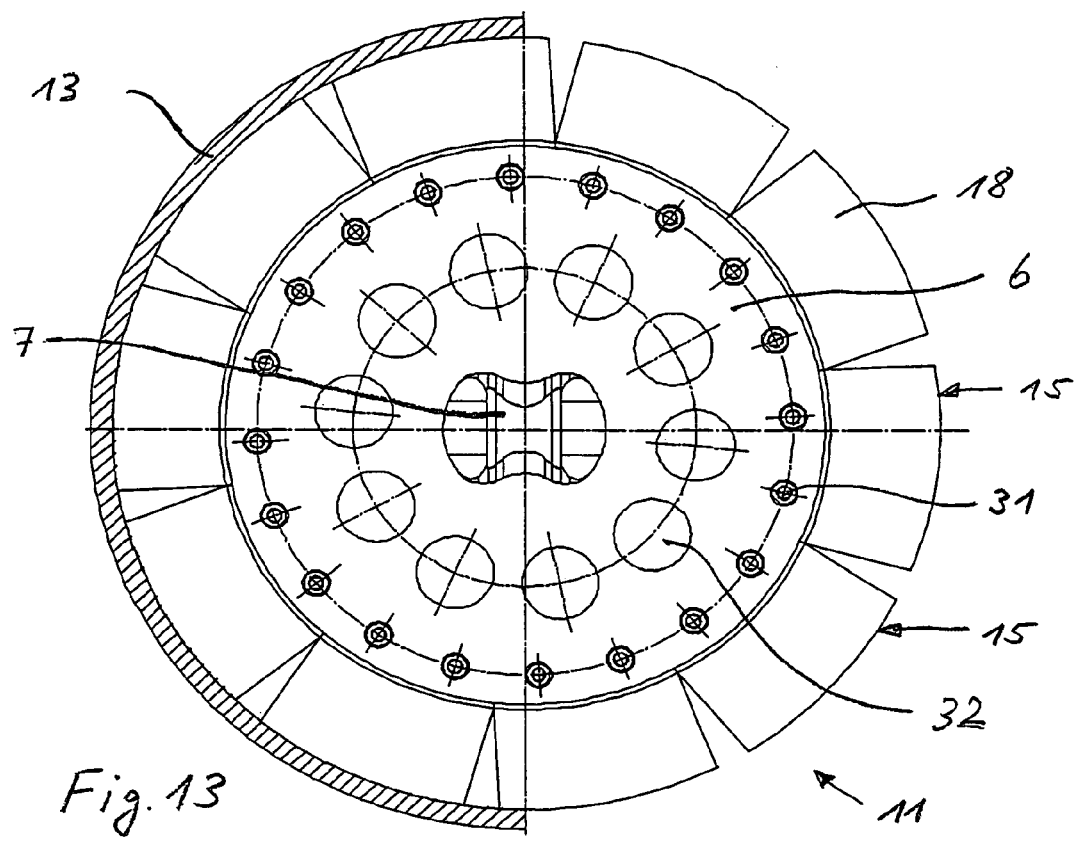
Figure 14:
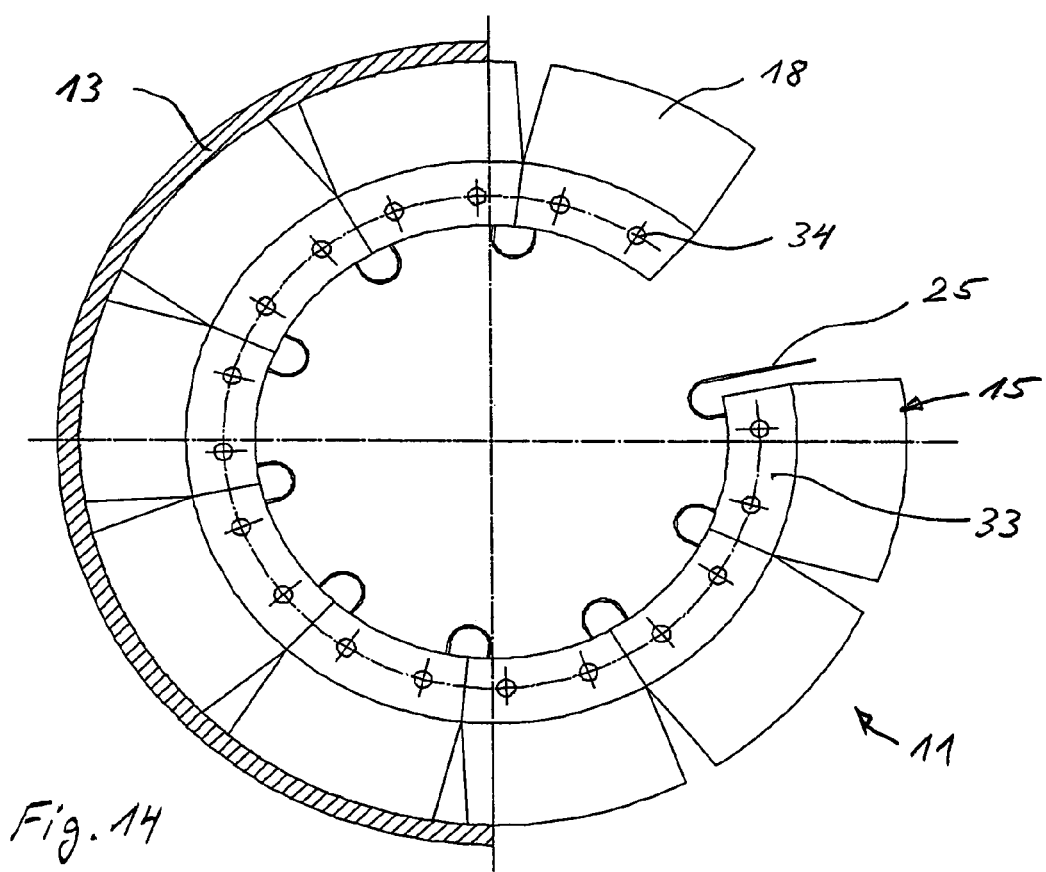
Figure 15:
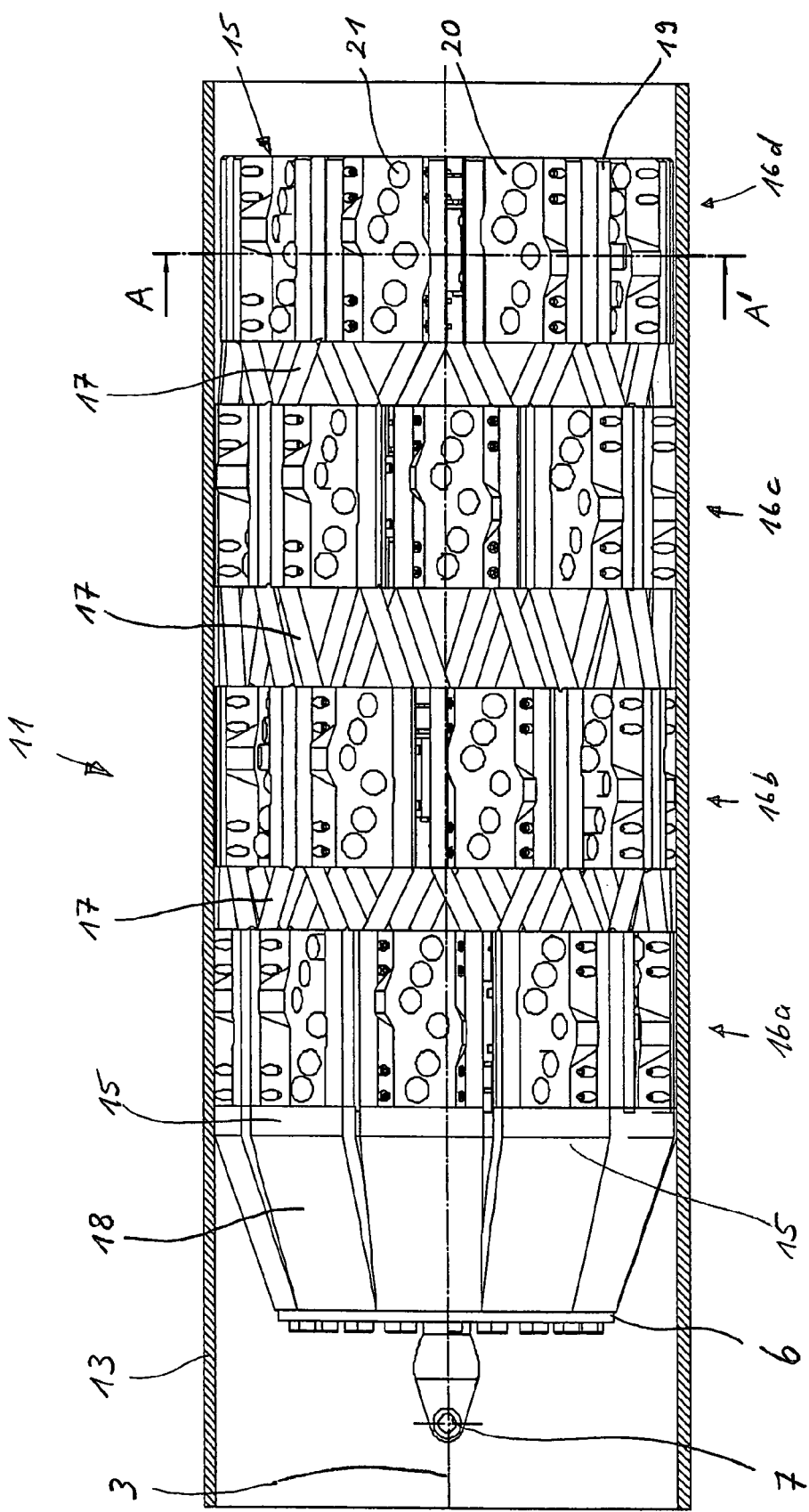
Figure 16:
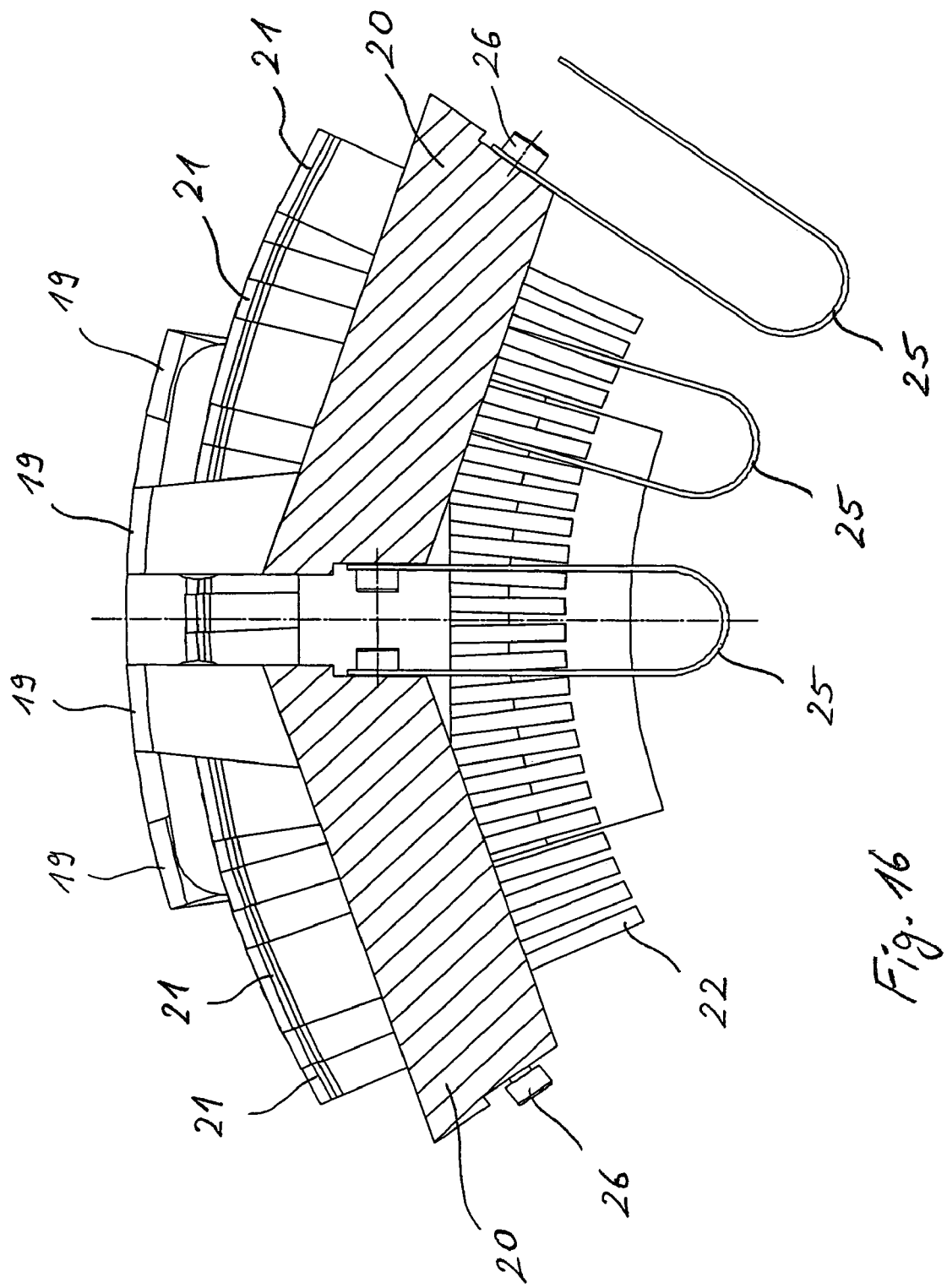
Figure 17:
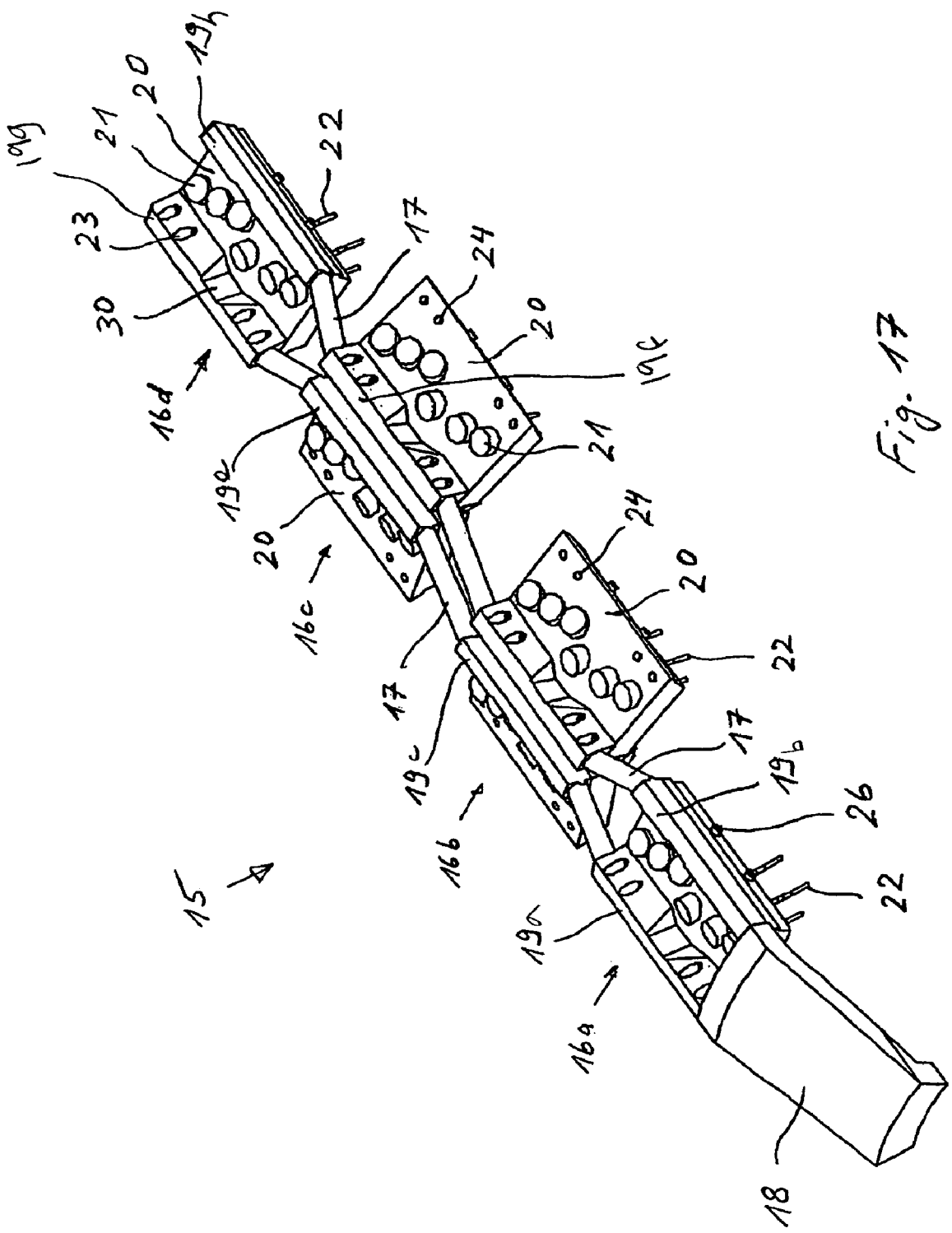
Figure 20:
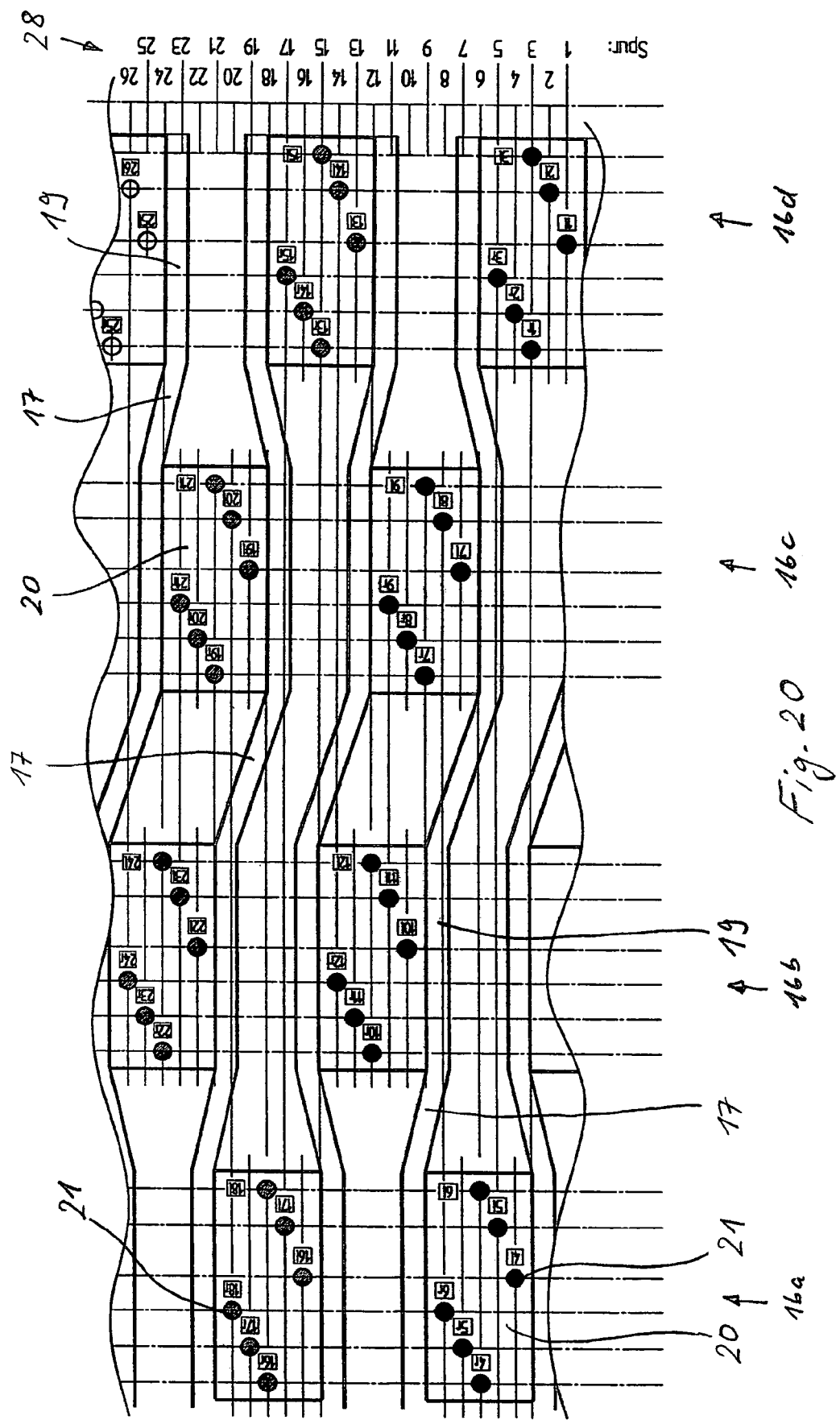
Figure 21:
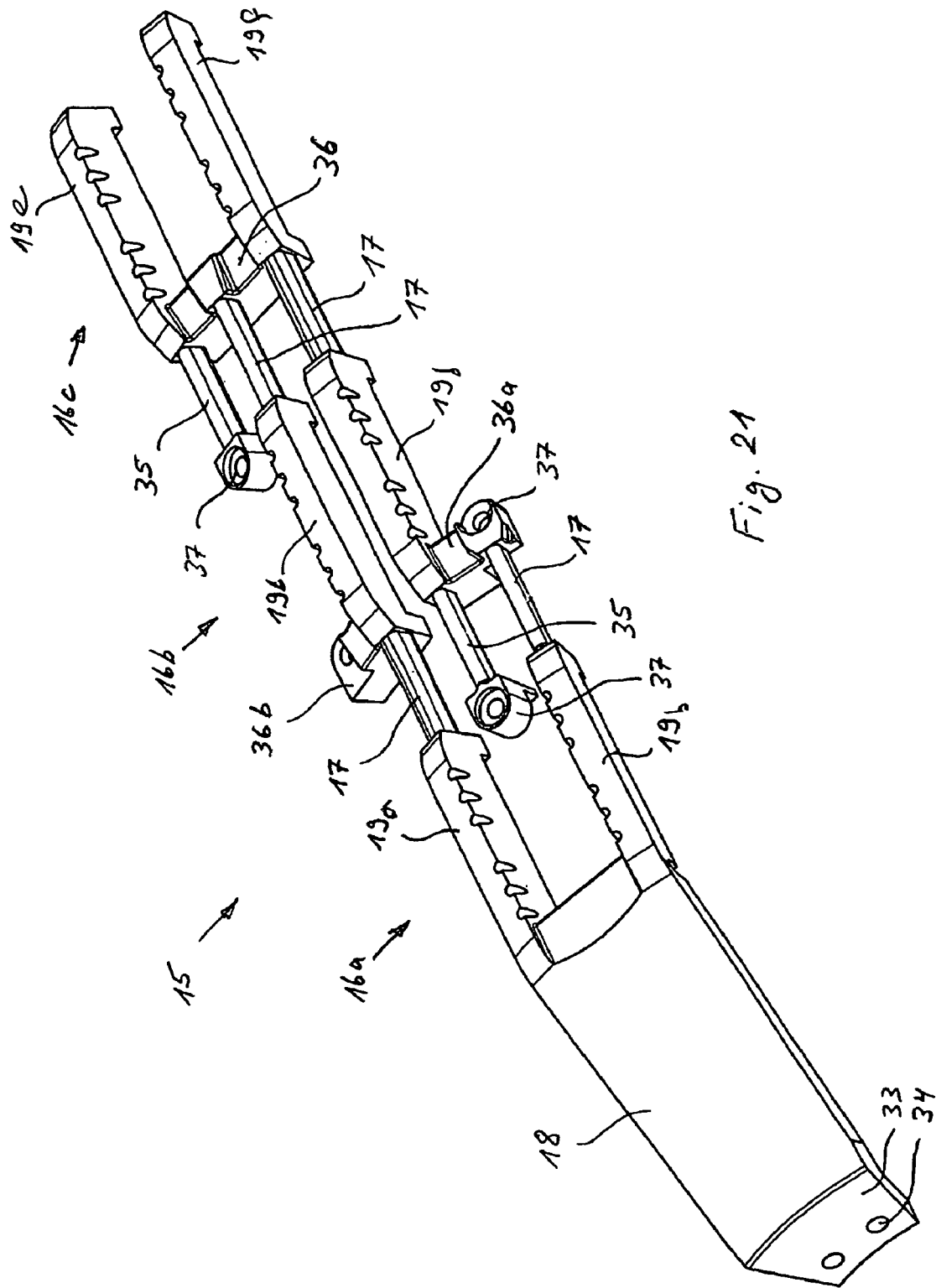
Figure 22:
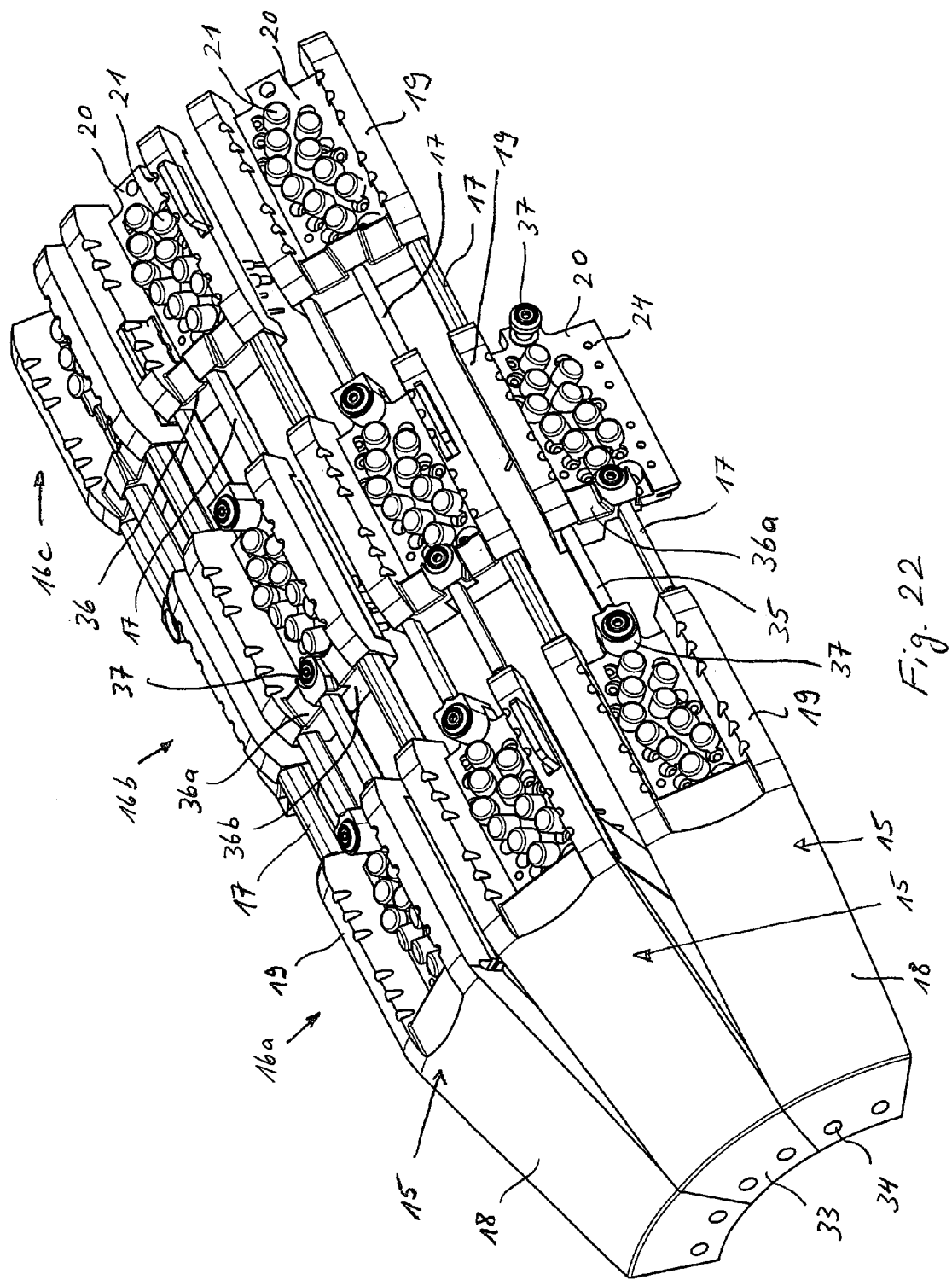
Figure 23:
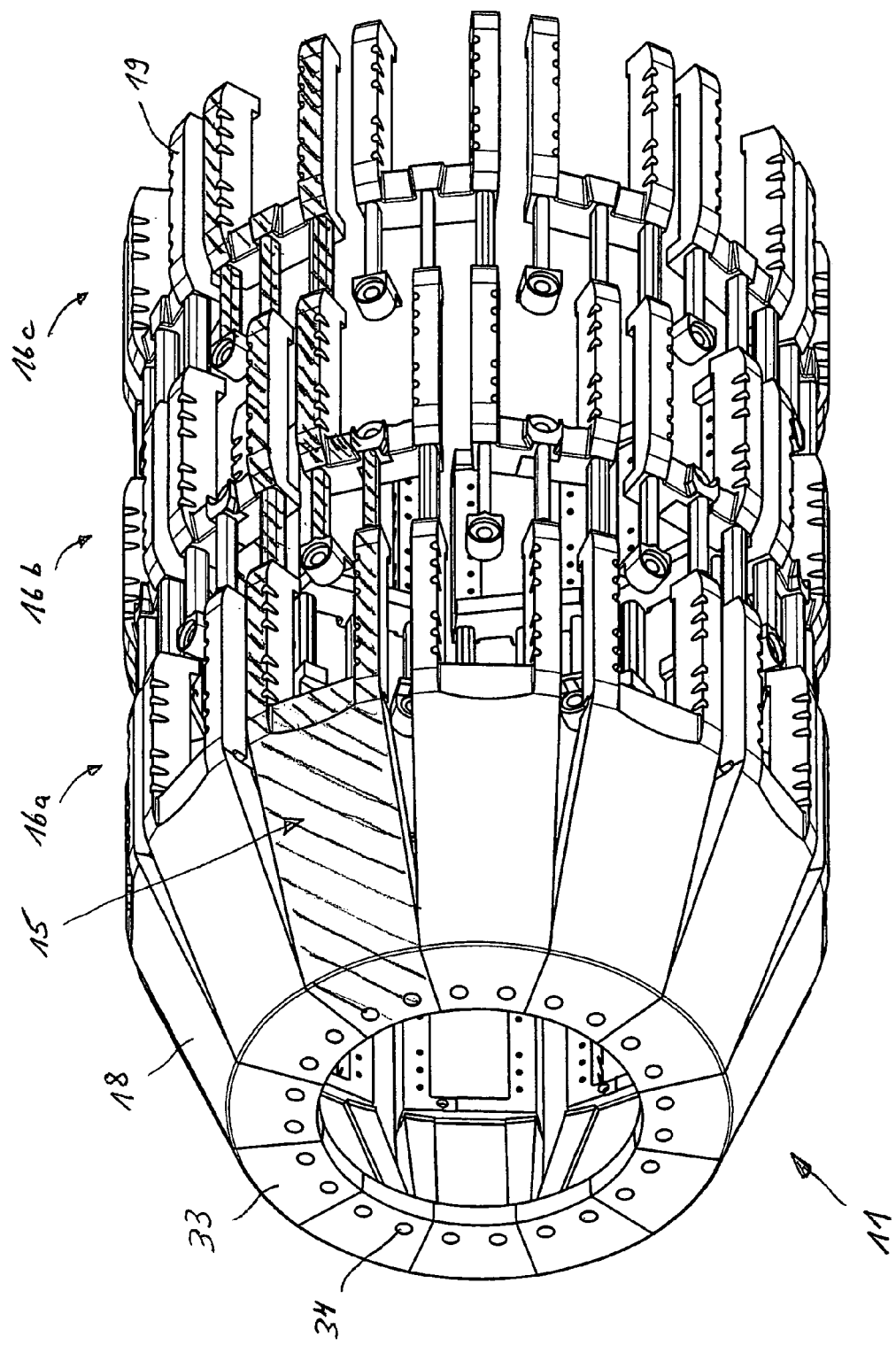
Figure 24:
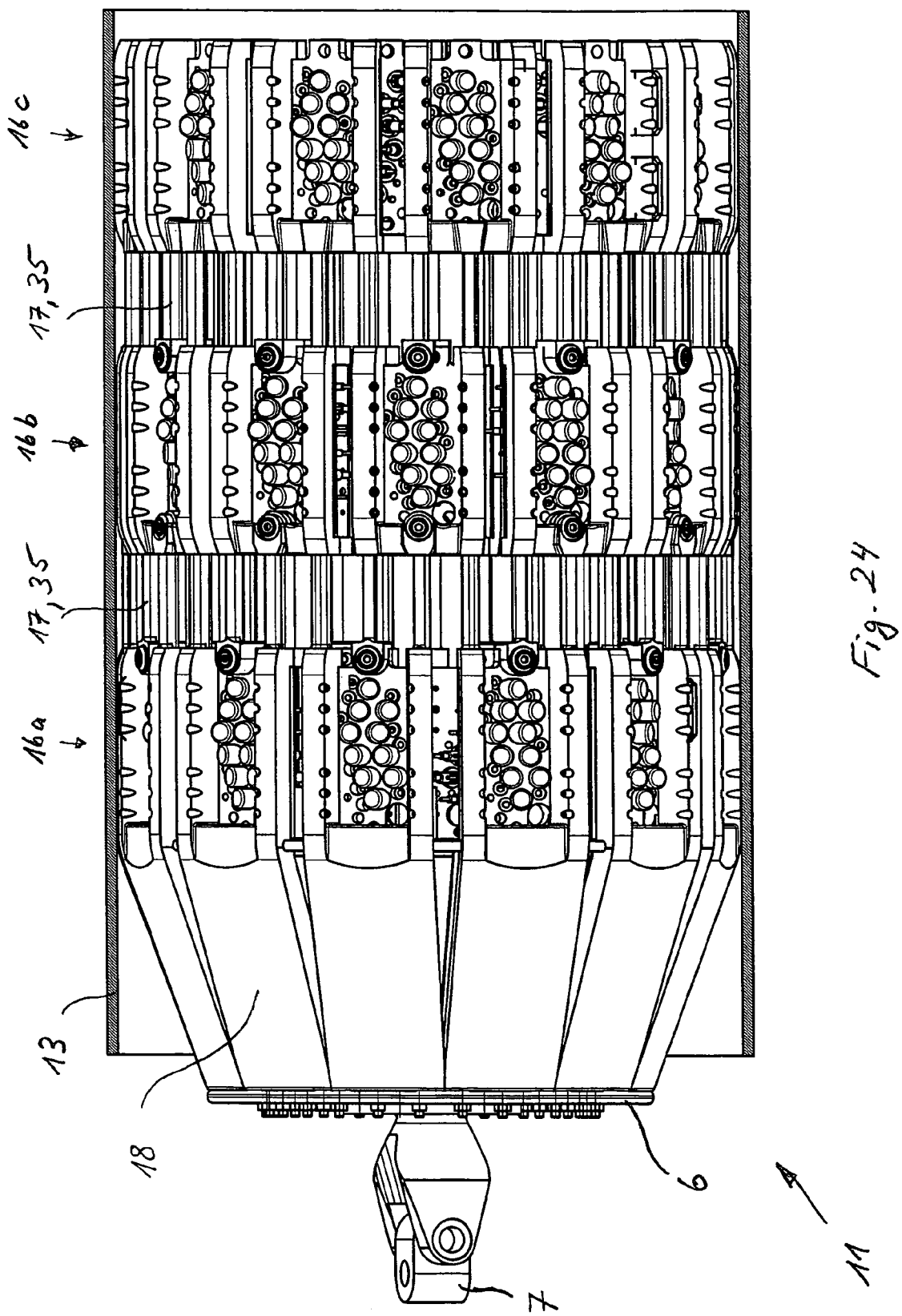
Figure 25:
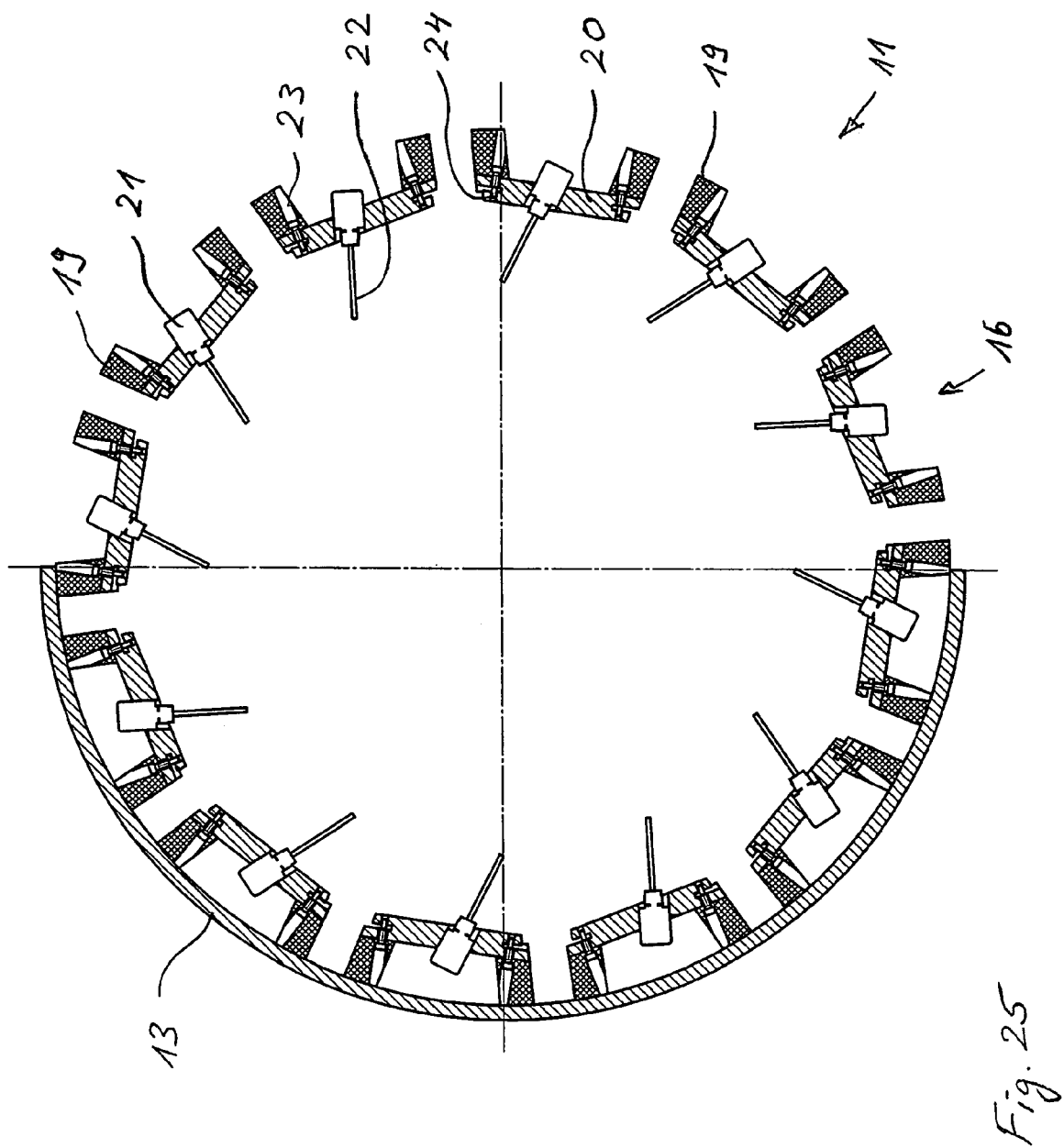
Figure 26:
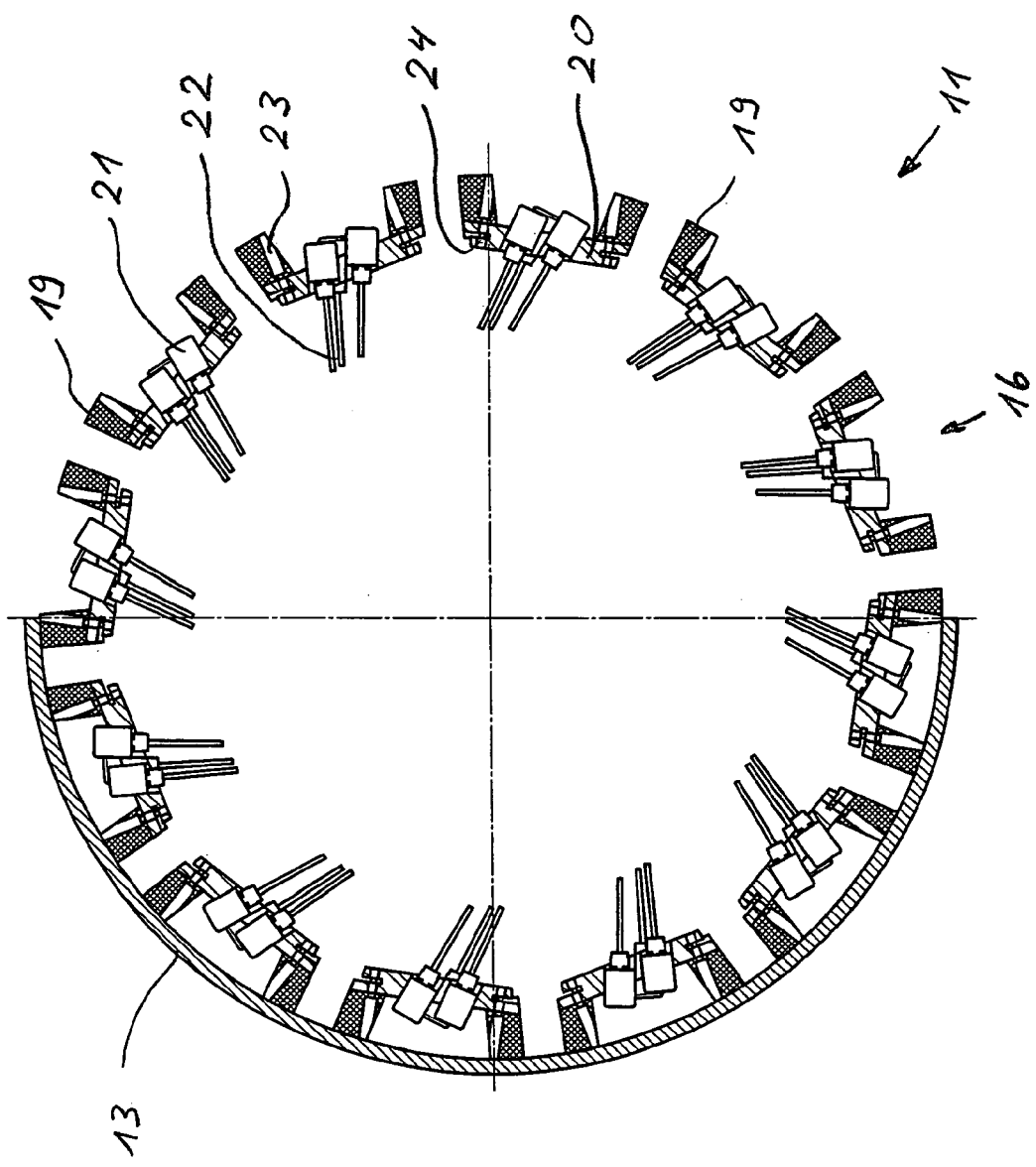
Figure 27:
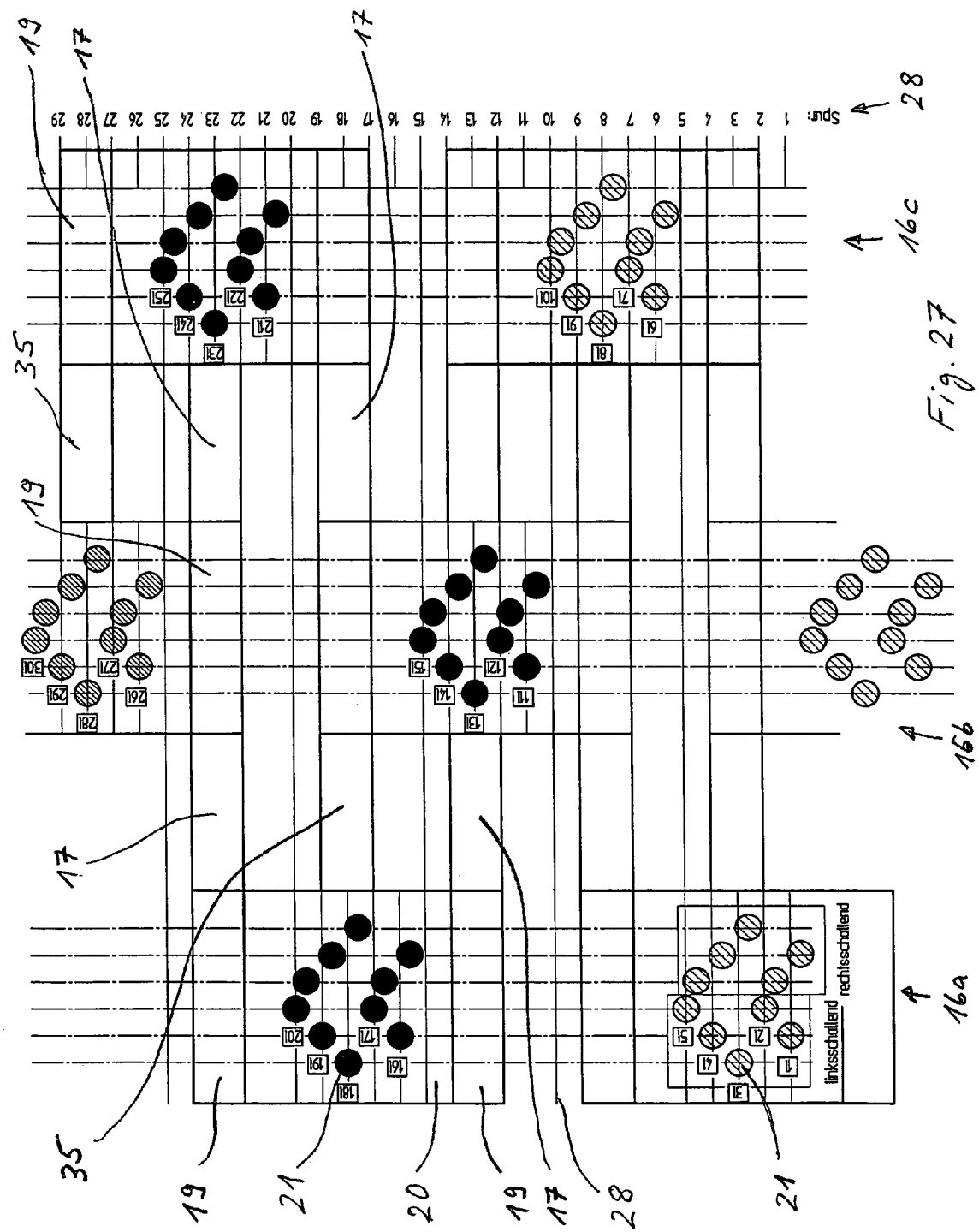

In the following, exemplary embodiments of known sensor-supporting elements are illustrated on the basis of two figures. The exemplary embodiments shown in the subsequent figures illustrate the invention. In the figures:

FIG. 1 shows a schematic side view of a known sensor-supporting element with twisted runners, FIG. 2 shows a schematic side view of another known sensor-supporting element with two segment rings formed by strip segments, FIG. 3 shows a side view of a section of a scraper-type device with a first sensor-supporting element according to the invention, and another scraper-type device element, FIG. 4 shows a perspective view of a segment according to the invention with two pairs of runners of FIG. 3, FIG. 5 shows a side view of the segment of FIG. 4, FIG. 6 shows a top view onto the segment of FIG. 4, FIG. 7 shows a schematic top view onto a pair of runners of a segment according to FIG. 4 with indication of the motion tracks of the sensors, FIG. 8 shows a perspective view of a modified segment according to FIG. 4 with two pairs of runners with abrasion-resistant shoes, FIG. 9 shows a side view of a sensor-supporting element according to FIG. 3 with segments according to FIG. 4, FIG. 10 shows a section along the line, A–A', of FIG. 9, FIG. 11 shows a section along the line, B–B', of FIG. 9, FIG. 12 shows a section along the line, C–C', of FIG. 9, FIG. 13 shows the front side of the sensor-supporting element according to FIG. 9 with flange, FIG. 14 shows the front side of the sensor-supporting element of FIG. 9 without flange, FIG. 15 shows a side view of a second sensor-supporting element with segments with four pairs of runners, FIG. 16 shows a detailed view of a section along the line, A–A', of FIG. 15, FIG. 17 shows a perspective view of a segment with four pairs of runners of FIG. 15, FIG. 18 shows a side view of the segment of FIG. 17, FIG. 19 shows a top view of the segment of FIG. 17, FIG. 20 shows a schematic top view onto four pairs of runners of a segment with indication of the motion tracks of the sensors, FIG. 21 shows a perspective view of a third embodiment of a segment according to the invention with three pairs of runners, FIG. 22 shows a perspective view of three assembled segments according to FIG. 21, FIG. 23 shows a perspective view of a sensor-supporting element assembled from segments according to FIG. 21, FIG. 24 shows a side view of a sensor-supporting element according to FIG. 23, FIG. 25 shows a section of FIG. 24, FIG. 26 shows another section of FIG. 24, and FIG. 27 shows a schematic top view onto a pair of runners of a segment according to FIG. 21 with indication of the motion tracks of the sensors.

FIG. 1 shows schematically a known sensor-supporting element 1A assembled from strip segments 2 which are provided in the form of runners which are twisted around the longitudinal axis of the sensor-supporting element 1 and extend at an acute angle to the middle axis 3 of the sensor-supporting element 1. Bores 4 for receiving sensors are provided in the strip segments 2. At its front side, the sensor-supporting element 1 comprises a conical-tapering strip section 5. The strip segments 2 are screwed to each other by means of a flange 6. In central position on the flange 6, a coupling part 7 is provided which serves for connection to other scraper-type device elements and preferably is provided in the form of a cardan joint.

During the movement of such a sensor-supporting element 1 through a pipeline, restoring forces act on the twisted strip segments 2 in the direction of a parallel alignment relative to the middle axis. Moreover, the sensor-supporting element 1 has a fixed length as a result of its design. This results in poor arc-traversing properties when traversing arcs with small pipe diameters. In practical application, the radii of curvature to be traversed by a scraper-type device are up to 1.5-fold the pipeline diameter. Consequently, the application of the known scraper-type device with pre-determined overall length is limited to larger pipeline diameters.

FIG. 2 shows schematically another known sensor-supporting element 1B, which comprises two sequentially arranged segment rings 8, which are assembled from strip segments 2, which are aligned parallel to the direction of motion and connected to each other by means of a rigid axis 9. Bores 4 for receiving sensors are provided in the strip segments 2. The strip segments 2 are connected at the conical-tapering strip sections 5 by means of a flange 6. Axis 9 bears cuffs 10 for guidance and a coupling part 7 for connecting to other scraper-type device elements at its ends and at its front side, respectively.

FIG. 3 shows in a longitudinal section of a pipeline 13 a side view of a first embodiment of a sensor-supporting element 11 according to the invention and another scraper-type device element 12 which is connected by means of a coupling part 7 with a cardan-type joint. The sensor-supporting element 11 is assembled from segments 15, which each comprise two sequentially arranged parallel pairs of runners 16. The scraper-type device element 12 can support for example measuring value recording devices or a power supply unit, and is fitted with two cuffs 10 touching the internal pipe wall.

Complementing FIG. 3, FIG. 4 shows a perspective view of a segment 15 according to the invention with two sequentially arranged pairs of runners (i.e., a first pair of runners 16a arranged sequentially with a second a second pair of runners 16b), which are connected by two converging elastic interim segments 17. As shown in FIG. 4, the first pair of runner 16a consists of runners 19a and 19b, and the second pair of runner 16a consists of runners 19c and 19d. At the front side in the direction of motion of the scraper-type device, the segment 15 is provided in the form of a truncated cone envelope as conical segment section 18. At its front side, conical-tapering segment section 18 is angled suitably to allow a flange to be connected.

A support plate 20 fitted with sensors 21 is attached between the runners 19 of the first (in the direction of motion of the scraper-type device) pair of runners 16a. The sensors 21 are attached to the support plate 20 such that the sensor connectors 22 (e.g. pins or plug connectors) protrude from the underside of the support plate 20. The sensors 21 can be aligned orthogonal or skewed relative to the internal pipe wall depending on the application purpose and measured value.

The runners 19 preferably have a trapezoidal cross-section and comprise bores 24 which are accessible via orifices 23 and serve to receive screws which are used to attach the support plates 20 to the runners 19.

U-shaped spring plates 25 are attached to the lateral surfaces of the support plates 20 by means of screws 26. One support plate 20 is screwed to each runner 19 of the second pair of runners 16b, and said support plate 20 in turn is screwed to the runners 19 of neighboring pairs of runners 16 of neighboring segments 15 during the assembly of such segments 15 to form a sensor-supporting element 11.

FIG. 5 and FIG. 6 show a side view of and a top view onto the segment 15 of FIG. 4, respectively. The segment 15 is essentially axially symmetrical to middle axis 27.

FIG. 7 illustrates in the form of a schematic developed view the tracks of motion 28 of the sensors 21, which are fitted on the support plates 20 between the pairs of runners 16 and between the neighboring runners 19 of neighboring pairs of runners 16. The tracks of motion 28 of all sensors 21 are equidistant parallel straight lines which ensures that the effective scanning areas of sensors 21 completely cover the internal pipe wall. The sensors 21 with neighboring tracks of motion 28 are usually arranged on one support plate 20.

FIG. 8 shows a perspective view of a segment 15 according to the invention with two pairs of runners 16. Two abrasion-resistant shoes 29, which end flush with the surface of the runners 19, are incorporated into each runner 19. The figure indicates how the abrasion-resistant shoes 29 are surrounded by casted material. In addition, the figure shows the recesses 30 in the runners 19, which provide clearance for sensors 21 emitting sound sideways.

FIG. 9 shows a side view of the sensor-supporting element 11 according to the invention in a longitudinal section of a pipeline 13. The sensor-supporting element 11 is assembled from segments 15, which each comprise sequentially arranged pairs of runners 16 with parallel runners 19. The pairs of runners 16 are connected by means of elastic diverging interim segments 17. The conical-tapering segment sections 18 of segments 15 form a truncated cone. They are kept together by means of a flange 6, which is attached at the front side by means of flange nuts. The middle of the flange 6 comprises a coupling part 7 which can be used to affix the sensor-supporting element 11 to another scraper-type device element.

FIG. 10 shows a section along the line, A-A', of the sensor-supporting element 11 according to the invention shown in FIG. 9. Similar to other figures, the pipeline 13, whose internal wall corresponds to the cylindrical envelope surface of the sensor-supporting element 11, is shown only in one half of the figure for purposes of clarity. The support plates 20, which are fitted with sensors 21, are attached between one runner of one pair of runners and a neighboring runner of a neighboring pair of runners. For example, as illustrated in FIG. 20, runners 19w and 19x form a pair of runners and runners 19y and 19z form a pair of runners that neighbor runners 19w and 19x, and support plate 20a is attached between runners 19x and 19y. Between the support plates 20, U-shaped spring plates 25 are attached with screws to the lateral surfaces of the support plates. The spring plates 25 effect pretensioning of the sensor-supporting element 11 such that the runners 19 firmly touch the internal pipe wall of the pipeline 13.

FIG. 11 shows a section along the line, B–B', and FIG. 12 shows a section along the line, C–C', of the sensor-supporting element 11 according to the invention shown in FIG. 9.

FIG. 13 shows the front side of a sensor-supporting element 11. The conical-tapering segment sections 18 of the segments 15 are kept together by a circular flange 6 which is attached by means of screws 31. The circular flange 6 comprises orifices 32 through which cables can be passed. A coupling part 7 is attached in the middle of the circular flange 6.

FIG. 14 shows the front side of a sensor-supporting element 11 without showing the flange 6, which is attached to the conical-tapering segment sections 18, and without showing one segment 15. The conical-tapering segment sections 18 are arranged in rows forming a ring and form a ring-shaped level flange-receiving surface 33 at their front side. Thread bores 34 for the flange screws 31 are provided in the flange-receiving surface 33.

FIG. 15 shows the lateral view of a second sensor-supporting element 11 in a longitudinal section of a pipeline 13, such as is preferably used for crack testing. The sensor-supporting element 11 is assembled from segments 15 with four pairs of runners 16a, 16b, 16c, 16d each, which are connected by means of converging, parallel, and diverging elastic interim elements 17.

FIG. 16 shows a detail of a section along the line, A–A', of FIG. 15. Sensors 21 are attached to the support plates 20, which are connected to U-shaped spring plates 25, such that the sensor connectors 22 protrude on the underside of the support plate 20.

FIG. 17 shows a perspective view of a segment 15 according to the invention of FIG. 15 with four sequentially arranged parallel pairs of runners 16a, 16b, 16c, 16d, whereby support plates 20 for sensors 21 are attached between the first pair of runners 16a and between the fourth pair of runners 16d. As shown in FIG. 17, the third pair of runners 16c consists of runner 19e and 19f, and the fourth pair of runners 16d consists of runner 19g and 19h. One support plate 20 each is attached to each runner 19 of the second and the third pair of runners 16b, 16c and can be connected to a runner of the neighboring segment. The first and the second pair of runners 16a, 16b are connected by means of converging interim elements 17, the second and the third pair of runners 16b, 16c are connected by means of parallel interim elements 17, and the third and the fourth pair of runners 16c, 16d are connected by means of diverging interim elements 17, whereby all said interim elements 17 engage the runners 19 at an angle.

FIG. 18 and FIG. 19 show a side view of and a top view onto the segment 15 of FIG. 17, respectively. The third and the fourth pair of runners 16c, 16d are arranged laterally offset from the middle axis 27 of the first and the second pair of runners 16a, 16b, such that the adjacent effective scanning areas of the sensors 21 of different support plates 20 complement each other. This also provides for high measuring accuracy as is required for pipeline crack testing.

FIG. 20 illustrates the tracks of motion 28 of the sensors 21 in the form of a schematic developed view complementing FIG. 15. The number and arrangement of the sensors 21 and the offset of the support plates 20 in the direction of the circumference provide for two sensors 21 of different support plates 20 each to have the same track of motion 28. The effective scanning area of the sensors 21 on the same track of motion 28 thus overlap, for example in order to achieve higher measuring accuracy. However, the sensors 21 can also emit sound in different directions, e.g. left versus right, for example for crack testing.

FIG. 21 shows another advantageous embodiment of a segment 15 according to the invention, which is provided to have special stability with regard to strong pulling forces. It comprises three sequentially arranged pairs of runners 16a, 16b, 16c with two parallel runners 19 each. For example, the pair of runners 16c consists of runners 19e and 19f. The segment 15 is provided to be conical-tapering at its front side.

Unlike the embodiments of FIGS. 8 and 17, the interim elements 17 between sequentially arranged runners 19 are oriented in the direction of motion of the scraper-type device and consequently no transverse forces act on these interim elements 17. Moreover, in this embodiment additional connecting elements 35 extending in longitudinal direction are provided which are connected between runners 19 and support plates 20 (see FIG. 22) such as to carry weight. The one interim element 17 between the first pair of runners 16a and the second pair of runners 16b extends straight between the sequentially arranged runners 19 of the pairs of runners 16a, 16b. The other interim element 17 between the first pair of runners 16a and the second pair of runners 16b is connected by means of a transverse fin part 36a, at which the interim element 17 is attached by means of a sleeve 37, to a parallel, laterally offset runner 19 of the second pair of runners 16b.

This laterally offset runner 19 of the second pair of runners 16b comprises in the direction of the conical-tapering segment section 18 a connecting element 35, which is provided with a sleeve 37, to which a support plate 20, which is part of the first pair of runners 16a, can be attached. In addition, this runner 19 is connected to a runner 19 of the third pair of runners 16c in a straight connection by means of an interim element 17. The other runner 17 of the second pair of runners 16b comprises at its front side a transverse fin part 36b, which is suitable to receive a sleeve 37 of an interim element 17 and a transverse fin part 36a of a neighboring segment 15. It is connected in a straight connection by means of an interim element 17 to a transverse fin 36, which is attached between and at the front side of the runners 19 of the third pair of runners 16c.

The function of corresponding assembled transverse fin parts 36a, 36b corresponds to the function of a transverse fin 36. The runner 19 of the third pair of runners 16c, which is not connected in a straight connection to a runner 19 of the second pair of runners 16b, comprises at its front side a connecting element 35, which is provided with a sleeve 37, to which a support plate 20 can be attached.

If one support plate 20 each is connected to the first pair of runners 16a and the third pair of runners 16c, then, when the sensor-supporting element is pulled through a pipeline, there is a straight flux of force from the one runner 19 of the first pair of runners 16a to the transverse fin 36 of the third pair of runners 16c, and another straight flux of force from the support plate 20 between the first pair of runners 16a via the connecting element 35, which is attached to the support plate 20 by means of a sleeve 37 and which connects the support plate 20 to the runner 19 of the second pair of runners 16b, to the one runner 19 of the third pair of runners 16c. The same applies to the support plate 20, which is attached to the second pair of runners 16b and provides for the connection to a neighboring segment.

By these means, the segment 15 and the sensor-supporting element assembled from such segments attain very high stability and sensor steering stability even in the presence of strong pulling forces.

FIG. 22 shows in a section of a sensor-supporting element three assembled segments 15 according to FIG. 21, in which a support plate 20 each is attached between the first pair of runners 16a and the third pair of runners 16c. Moreover, another support plate 20 is attached between each runner 19 of the second pair of runners 16b of a segment 15 and the neighboring runner 19 of the second pair of runners 16b of the neighboring segment 15. The compact and highly stable design is evident from this figure, which still allows the implementation of a multitude of sensors 21, including those with overlapping tracks of motion, especially on different support plates 20. The U-shaped spring plates between neighboring runners 19 are not shown in the figure for purposes of clarity.

FIG. 23 shows a sensor-supporting element 11 assembled from segments 15 according to FIG. 21. The support plates 20 are not shown in this figure for purposes of clarity. In addition, one segment 15 is indicated by hatching to clarify the structure and modular assembly from identical segments 15 according to FIG. 21.

FIGS. 24 to 27 are further representations of the sensor-supporting element 11 according to FIG. 23. FIG. 24 corresponds to FIG. 9, and FIGS. 25 and 26 correspond to FIGS. 10 to 12, with the U-shaped spring plates not being shown, and FIG. 27 corresponds to FIG. 20.

LIST OF REFERENCE NUMBERS

1 Known sensor-supporting element
2 Strip segment
3 Middle axis of the sensor-supporting element
4 Bore for sensor
5 Conical-tapering strip section
6 Flange
7 Coupling part
8 Segment ring
9 Rigid axis
10 Cuff
11 Sensor-supporting element according to the invention
12 Scraper-type device element
13 Pipeline
15 Segment according to the invention
16 Parallel pair of runners
16a First pair of runners
16b Second pair of runners
16c Third pair of runners
16d Fourth pair of runners
17 Elastic interim element
18 Conical-tapering segment section
19 Runner
20 Support plate
21 Sensor
22 Sensor connector
23 Orifice in a runner
24 Thread bore in a support plate
25 U-shaped spring plate
26 Attachment screw of a U-shaped spring plate
27 Middle axis of a pair of runners
28 Track of motion of a sensor
29 Abrasion-resistant shoe
30 Recess
31 Flange screw
32 Orifice
33 Flange receiving surface
34 Thread bore for flange screw
35 Connecting element
36 Transverse fin
36a First transverse fin part
36b Second transverse fin part
37 Sleeve

The invention claimed is:

1. Segment (15) of a sensor-supporting element (11) of a scraper-type device, in which the sensor-supporting element (11) is assembled from such segments (15) and forms a hollow body with a cylindrical envelope surface and the scraper-type device can be moved through a pipeline (13) for the purpose of pipeline testing, whereby the sensor-supporting element (11) is fitted with sensors (21) required for the performance of the pipeline testing, characterized in that:
the segment (15) comprises at least a first pair of essentially parallel runners (19a, 19b) and a second pair of essentially parallel runners (19c, 19d), whereby the at least two pairs of runners are sequentially arranged relative to the direction of motion of the scraper-type device;

the first pair of runners (19a, 19b) are elastically connected to the second pair of runners (19c, 19d) by connecting elements (17);

a sensor plate (20) for sensors (21) is arranged between and connected to the first pair of runners (19a, 19b); and the segment (15) is adapted such that it can be connected to additional such segments (15) by means of a connecting device connecting the segments (15) so as to form the hollow body with a cylindrical envelope surface.

2. Segment (15) according to claim 1, further comprising a second support plate (20) for sensors (21), wherein the second support plate (20) is attached between one of said runners of said second pair of runners (19c, 19d) and a runner of a neighboring segment (15).

3. Segment (15) according to claim 1, characterized in that the number of its pairs of runners (16) consisting of two parallel runners (19) each is between 2 and 10.

4. Segment (15) according to claim 1, characterized in that it comprises a conical-tapering segment section (18) at its front side facing in the direction of motion of a scraper-type device such that the hollow body assembled from such segments (15) is provided to be truncated cone-shaped at its front side facing in the direction of motion of the scraper-type device.

5. Segment (15) according to claim 1, characterized in that connecting elements are provided between sequential runners (19) of a segment (15) in the form of twin-diverging or -converging elastic interim segments (17) connecting sequential runners (19).

6. Segment (15) according to claim 1, characterized in that the interim segments (17) are between 2 cm and 50 cm in length.

7. Segment (15) according to claim 1, characterized in that each said runner is between 5 cm and 300 cm in length.

8. Segment (15) according to claim 1, characterized in that the cross-section of the runners (19) is trapezoidal, parallelogram-like or rectangular.

9. Segment (15) to claim 1, characterized in that the runners (19) comprise recesses (30).

10. Segment (15) to claim 1, characterized in that the support plates (20) for the sensors (21) have a substantially smooth topside.

11. Segment (15) to claim 1, characterized in that the undersides of the runners (19) are bevelled such that they are adapted to the orientation of a support plate (20) to be attached.

12. Segment (15) to claim 1, characterized in that the runners (19) consist of an elastic material.

13. Segment (15) to claim 1, characterized in that the segment (15) is provided fully or essentially in the form of a single part comprising one or several of the following components: runners (19), connecting elements (35), interim segments (17), conical-tapering segment section (18), transverse fin (36), transverse fin part (36a, 36b).

14. Segment (15) according to claim 1, characterized in that the number of its pairs of runners (16) consisting of two parallel runners (19) each is between 2 and 4.

15. Segment (15) according to claim 1, characterized in that each said runner (19) is between 10 cm and 50 cm in length.

16. Segment (15) according to claim 1, characterized in that the connecting device, which can be used to connect the segment to other such segments (15) to form a hollow body with a cylindrical envelope surface, can be attached to the front side of the segment (15) facing in the direction of motion of the scraper-type device.

17. Segment (15) according to claim 16, characterized in that the connecting device is provided in the form of a flange (6).

18. Segment (15) according to claim 1, characterized in that connecting elements are provided between sequential runners (19) of a segment (15) in the form of parallel elastic interim segments (17) connecting sequential runners (19).

19. Segment (15) according to claim 18, characterized in that the elastic interim segments (17) are attached at an angle to the runners (19) they connect.

20. Segment (15) according to claim 18, characterized in that the elastic interim segments (17) have a round, oval, rectangular or trapezoidal cross-section.

21. Segment (15) according to claim 18, characterized in that the cross-section of the elastic interim segments (17) is smaller than the cross-section of the runners (19).

22. Segment (15) according to claim 18, characterized in that the ratio of the length of the elastic interim segments (17) and the length of the adjacent runners (19) connected by them is between 1/10 and 5.

23. Segment (15) according to claim 18, characterized in that the ratio of the length of the elastic interim segments (17) and the length of the adjacent runners (19) connected by them is between 2/10 and 1.

24. Segment (15) according to claim 1, characterized in that it comprises at its front side facing in the direction of motion of the scraper-type device and between at least one pair of runners (16) a transverse fin (36, 36a, 36b) connecting the runners (19) of the pair of runners (16).

25. Segment (15) according to claim 24, characterized in that it comprises between sequential runners (19) an interim element (17), one end of which is connected to a trailing pair of runners (19) by means of a tranverse fin part (36a).

26. Segment (15) according to claim 25, characterized in that the interim element (17) is linked to the transverse fin part (36a) by means of a sleeve (37).

27. Segment (15) according to claim 1, characterized in that it comprises between the support plate (20), which is attached between a pair of runners (16) and a runner (16) of a trailing pair of runners (16) with regard to the motion of direction of the scraper-type device, a connecting element (35) connecting the support plate (20) and the runner (19).

28. Segment according to claim 27, characterized in that the connecting element (35) is arranged along the longitudinal direction of the runner (19).

29. Segment (15) according to claim 27, characterized in that the connecting element (35) between a support plate (20) and a runner (19) can be attached to the support plate (20) by means of a sleeve (37).

30. Segment (15) according to claim 1, characterized in that it comprises a transverse fin part (36a, 36b), which allows it to be connected to a neighboring segment (15).

31. Segment (15) according to claim 30, characterized in that the transverse fin part (36a, 36b) is provided such that it can be connected to a corresponding transverse fin part (36b, 36a) of a neighboring segment (15).

32. Segment (15) according to claim 1, characterized in that the surfaces of the upper sides of the runners (19) are arched transverse to the longitudinal direction of the runners (19).

33. Segment (15) according to claim 32, characterized in that the surfaces of the upper sides of the runners (19) are arched such that their radius of curvature is adapted to the radius of the cylindrical envelope surface of the hollow body assembled from such segments (15).

34. Segment (15) to claim 1, characterized in that metallic abrasion-resistant shoes (29) ending flush with the surface of the upper side of the runners (19) are incorporated into the runners.

35. Segment (15) according to claim 34, characterized in that between 1/10 and 3/4 of the length of a runner (19) are covered by incorporated abrasion-resistant shoes (29).

36. Segment (15) to claim 1, characterized in that it is provided such that the support plates (20) can be attached to the underside of the runners (19).

37. Segment (15) according to claim 36, characterized in that the runners (19) comprise bores for receiving screws such that support plates (20) fitted with internal threads (24) for the screws can be screwed to the underside of the runners (19).

38. Sensor-supporting element (11), provided in the form of a cylindrical hollow body, of a scraper-type element, which is assembled from multiple segments (15) according to claim 1.

39. Scraper-type element, characterized in that it comprises a sensor-supporting element (11) according to claim 38.

40. Sensor-supporting element (11) according to claim 38, characterized in that it comprises a connecting device connecting the segments (15) to form a hollow body with a cylindrical envelope surface.

41. Sensor-supporting element (11) according to claim 40, characterized in that the connecting device comprises a flange (6), which is arranged at the front side of the sensor-supporting element (11) facing in the direction of motion of the scraper-type device.

42. Sensor-supporting element (11) according to claim 40, characterized in that the connecting device comprises U-shaped spring plates (25), which are attached between neighboring segments (15).

43. Sensor-supporting element (11) according to claim 42, characterized in that the U-shaped spring plates (25) can be attached to the support plates (20).

44. Scraper-type element, characterized in that it comprises segments (15) according to claim 1.

* * * * *